United States Patent [19]

Meki et al.

[11] Patent Number: 4,837,236

[45] Date of Patent: Jun. 6, 1989

[54] FUNGICIDAL MORPHOLINE COMPOUNDS, AND THEIR PRODUCTION AND USE

[75] Inventors: Naoto Meki, Toyonaka; Hirotaka Takano, Nishinomiya, both of Japan

[73] Assignee: Sumitomo Chemical Company, Limited, Osaka, Japan

[21] Appl. No.: 100,461

[22] Filed: Sep. 24, 1987

[30] Foreign Application Priority Data

| | | |
|---|---|---|
| Sep. 24, 1986 [JP] | Japan | 61-225529 |
| Dec. 26, 1986 [JP] | Japan | 61-314251 |
| Feb. 12, 1987 [JP] | Japan | 62-30260 |
| Mar. 13, 1987 [JP] | Japan | 62-59166 |

[51] Int. Cl.$^4$ .................. A01N 43/84; C07D 295/06; C07D 295/08
[52] U.S. Cl. .................. 514/233.8; 514/238.2; 514/238.5; 514/239.5; 514/327; 514/317; 514/328; 514/331; 514/345; 544/148; 544/163; 544/167; 544/174; 546/216; 546/230; 546/236; 546/232; 546/330; 546/334; 546/338; 546/339
[58] Field of Search .............. 514/233.8, 238.2, 238.5, 514/239.2; 544/163, 167, 148, 174

[56] References Cited

U.S. PATENT DOCUMENTS 4,202,894   5/1980   Pfiffner ..................... 514/239.5

FOREIGN PATENT DOCUMENTS

| | | |
|---|---|---|
| 0007479 | 2/1980 | European Pat. Off. |
| 0066196 | 12/1982 | European Pat. Off. |
| 0074005 | 3/1983 | European Pat. Off. |
| 0129321 | 12/1984 | European Pat. Off. |
| 0142799 | 5/1985 | European Pat. Off. |
| 0193875 | 9/1986 | European Pat. Off. |
| 0209763 | 1/1987 | European Pat. Off. |
| 2752096 | 6/1978 | Fed. Rep. of Germany |
| 3001581 | 7/1981 | Fed. Rep. of Germany |
| 3019496 | 11/1981 | Fed. Rep. of Germany |
| 3019497 | 11/1981 | Fed. Rep. of Germany |
| 3034383 | 4/1982 | Fed. Rep. of Germany |
| 3126818 | 1/1983 | Fed. Rep. of Germany |
| 3134220 | 3/1983 | Fed. Rep. of Germany |
| 3215409 | 10/1983 | Fed. Rep. of Germany |
| 3321712 | 12/1984 | Fed. Rep. of Germany |
| 60-28973 | 2/1985 | Japan |
| 62-67069 | 3/1987 | Japan |
| 1591267 | 6/1981 | United Kingdom |

OTHER PUBLICATIONS

Konig et al, "Angew. Chem.", 77, pp. 327-333 (1965).

Primary Examiner—Mary C. Lee
Assistant Examiner—Mary Sue Howard
Attorney, Agent, or Firm—Birch, Stewart, Kolasch & Birch

[57] ABSTRACT

A heterocyclic compound of the formula:

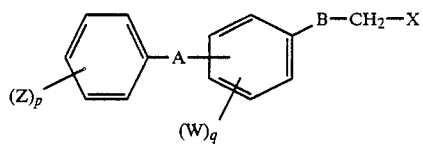

wherein
A is an oxygen atom or a sulfur atom;
B is either one of the groups: —CH$_2$—CHR$^1$— or —CH=CR$^1$— (in which R$^1$ is a hydrogen atom or a methyl group);
W is, the same or different, each a hydrogen atom, a halogen atom, a lower alkyl group or a lower alkoxy group;
X is either one of the following groups:

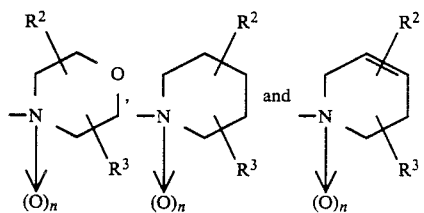

(in which R$^2$ is a hydrogen atom, a lower alkyl group, a lower alkoxy group, a lower alkoxy(lower)alkyl group, a hydroxyl group or a hydroxy(lower)alkyl group, R$^3$ is a hydrogen atom or a lower alkyl group and n is an integer of 0 or 1);
Z is, the same or different, each a hydrogen atom, a halogen atom, a lower alkyl group, a lower alkoxy group, a halo(lower)alkyl group, a halo(lower)alkoxy group, a nitro group, a methylenedioxy group or a cyano group;
p is an integer of 0 to 5; and
q is an integer of 0 or 1, or its salt, which is useful as a fungicide.

9 Claims, No Drawings

FUNGICIDAL MORPHOLINE COMPOUNDS, AND THEIR PRODUCTION AND USE

The present invention relates to heterocyclic compounds, and their production and use. More particularly, the invention relates to novel heterocyclic compounds having fungicidal activity, and their production and use.

The present heterocyclic compounds are representable by the formula:

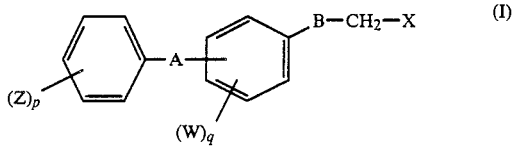

wherein
A is an oxygen atom or a sulfur atom;
B is either one of the groups: $-CH_2-CHR^1-$ or $-CH=CR^1-$ (in which $R^1$ is a hydrogen atom or a methyl group);
W is, the same or different, each a hydrogen atom, a halogen atom, a lower alkyl group or a lower alkoxy group;
X is either one of the following groups:

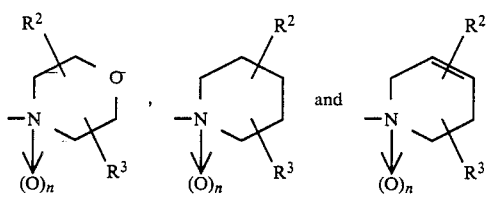

(in which $R^2$ is a hydrogen atom, a lower alkyl group, a lower alkoxy group, a lower alkoxy(lower)alkyl group, a hydroxyl group or a hydroxy(lower)alkyl group, $R^3$ is a hydrogen atom or a lower alkyl group and n is an integer of 0 or 1);
Z is, the same or different, each a hydrogen atom, a halogen atom, a lower alkyl group, a lower alkoxy group, a halo(lower)alkyl group, a halo(lower)alkoxy group, a nitro group, a methylenedioxy group or a cyano group;
p is an integer of 0 to 5; and
q is an integer of 0 or 1.

The salts of the invention cover acid addition salts, of which the acid portion may be chosen from inorganic acids (e.g. hydrochloric acid, sulfuric acid, nitric acid) and organic acids (e.g. formic acid, acetic acid, propionic acid, methanesulfonic acid, benzenesulfonic acid, p-toluenesulfonic acid).

Throughout the specification, the term "lower" is intended to mean any group having not more than 6 carbon atoms, preferably 1 to 4 carbon atoms. The term "halogen" encompasses usually chlorine, bromine, iodine and fluorine.

There are known a large number of compounds usable as fungicides. In general, however, they are required to be used in large doses to obtain prominent fungicidal properties. Further, it is frequently observed that their preventive effect is satisfactory yet their curative effect is insufficient. Furthermore, their antifungal spectrum is often not sufficiently broad. In addition, their continuous application over a long period of time develops resistance in fungi so that their preventive or curative effect is much diminished.

Some kinds of heterocyclic compounds are reported to have fungicidal activity [Angewandte Chemie, 77, 327 (1965); JP-A-68785/78; JP-A-68786/78; JP-A-77070/781]. Their fungicidal potency and antifungal spectrum, however, are not always sufficient.

In order to embody any compound having excellent fungicidal activity, various attempts have been made. As a result, it has now been found that the heterocyclic compounds of the formula (I) and their salts exhibit an appreciable fungicidal property. This invention is based on the above finding.

As state above, the heterocyclic compounds (I) and their salts exert appreciable fungicidal property. For instance, they exert preventive, curative and/or systemic effect against a wide variety of phytopathogenic fungi, of which typical examples are as follows: *Pyricularia oryzae, Cochliobolus miyabeanus* and *Rhizoctonia solani* on rice plants, *Erysiphe graminis* f. sp. *hordei, Erysiphe graminis* f. sp. *tritici, Gibberella zeae, Puccinia striiformis, Puccinia graminis, Puccinia recondita, Puccinia hordei,* Typhula sp., *Micronectriella nivalis, Ustilago tritici, Ustilago nuda, Tilletia caries, Pseudocercosporella herpotrichoides, Pyrenophora teres, Phynchosporium secalis, Septoria tritici* and *Leptosphaeria nodorum* on wheats and barleys, *Diaporthe citri, Eisinoe fawcetti, Penicillium digitatum* and *Penicillium italicum* on citrus fruits, *Sclerotinia mali, Valsa mali, Podosphaera leucotricha, Alternaria mali* and *Venturia inaequalis* on apples, *Venturia nashicola, Venturia pirina, Alternaria kikuchiana* and *Gymosporangium haraeanum* on pears, *Sclerotinia cinerea, Cladosporium carpophilum* and *Phomopsis* sp. on peaches, *Elsinoe ampelina, Glomerella cingulata, Uncinula necator, Phakopsora ampelopsidis* and *Guignardia bidwellii* on grapes, *Gloeosporium kaki, Cercospora kaki, Mycosphaerella nawae* on persimmons, *Colletotrichum lagenarium, Sphaerotheca fuliginea* and *Mycosphaerella melonis* on cucumbers, *Alternaria solani* and *Cladosporium fulvum* on tomatoes,

*Phomopsis vexans* and *Erysiphe cichoracearum* on eggplants, *Alternaria japonica* and *Cercosporella brassicae* on rapes, *Puccinia allii* on onions, *Cercospora kikuchii, Elsinoe glycines* and *Diaporthe phaseolorum* var. *sojae* on soybeans, *Colletotrichum lindemthianum* on kidney beans, *Mycosphaerella personatum,* and *Cercospora arachidicola* on peanuts, *Erysiphe pisi* on peas, *Alternaria solani* on potatoes, *Sphaerotheca humuli* on strawberries, *Exobasidium reticulatum* and *Elsinoe leucospila* on tea plants, *Alteria longipes, Erysiphe cichoracearum, Colletotrichum tabacum* on tobacco plants, *Cercospora beticola* on sugarbeets, *Diplocarpon rosae, Sphaerotheca pannosa* on roses, *Septoria chrysanthemi-indici* and *Puccinia horiana* on chrysanthemums, *Botrytis cinerea* and *Sclerotinia sclerotiorum* on various crop plants, etc.

Among the heterocyclic compounds (I), preferred are those of the formula:

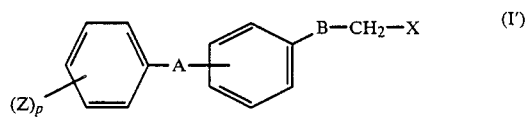

wherein
X is either one of the following groups:

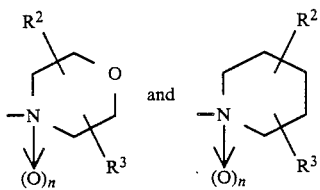

(in which $R^2$ is a hydrogen atom, a $C_1$-$C_2$ alkyl group, a $C_1$-$C_2$ alkoxy group, a $C_1$-$C_2$ alkoxy($C_1$-$C_2$)alkyl group, a hydroxyl group or a hydroxy($C_1$-$C_2$)alkyl group, $R^3$ is a hydrogen atom or a methyl group and n is an integer of 0 or 1);

Z is, the same or different, a hydrogen atom, a halogen atom, a $C_1$-$C_4$ alkyl group, a $C_1$-$C_2$ alkoxy group, a halo($C_1$-$C_2$)alkyl group, a halo($C_1$-$C_2$)alkoxy group, a nitro group, a methylenedioxy group or a cyano group;

p is an integer of 0 to 5; and

A and B are each as defined above.

More preferred are those of the formula (I') wherein

X is either one of the following groups:

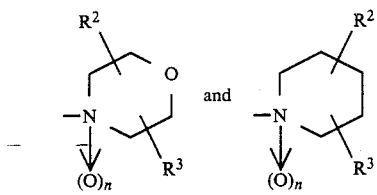

(in which $R^2$ is a hydrogen atom, a $C_1$-$C_2$ alkyl group, a $C_1$-$C_2$ alkoxy group or a $C_1$-$C_2$ alkoxy($C_1$-$C_2$)alkyl group, $R^3$ is a hydrogen atom or a methyl group and n is an integer of 0 or 1);

Z is, the same or different, a hydrogen atom, a halogen atom, a $C_1$-$C_4$ alkyl group, a methoxy group, a trifluoromethyl group, a halo($C_1$-$C_2$)alkoxy group, a nitro group, a methylenedioxy group or a cyano group;

p is an integer of 0 to 5; and

A and B are each as defined above.

The most preferred are those of the formula (I') wherein

X is either one of the following groups:

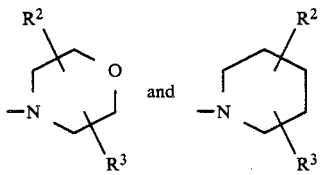

(in which $R^2$ is a hydrogen atom, a $C_1$-$C_2$ alkyl group, a $C_1$-$C_2$ alkoxy group or a $C_1$-$C_2$ alkoxy($C_1$-$C_2$)alkyl group and $R^3$ is a hydrogen atom or a methyl group);

Z is, the same or different, a hydrogen atom, a halogen atom, a $C_1$-$C_4$ alkyl group, a methoxy group, a trifluoromethyl group, a halo($C_1$-$C_2$)alkoxy group, a nitro group, a methylenedioxy group or a cyano group;

p is an integer of 0 to 5; and

A and B are each as defined above.

Particularly preferred are those of the formula (I') wherein

X is either one of the following groups:

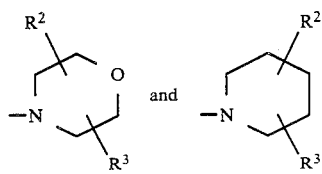

(in which $R^2$ is a hydrogen atom or a $C_1$-$C_2$ alkyl group and $R^3$ is a hydrogen atom or a methyl group);

A is an oxygen atom or a sulfur atom;

Z is, the same or different, a hydrogen atom, a $C_1$-$C_4$ alkyl group, a methoxy group, a trifluoromethyl group, a halo($C_1$-$C_2$)alkoxy group, a nitro group, a methylenedioxy group or a cyano group;

p is an integer of 0 to 5; and

A and B are each as defined above.

The heterocyclic compounds (I) can be prepared by various procedures, of which typical ones are shown below:

Procedure (1)

A heterocyclic compound of the formula:

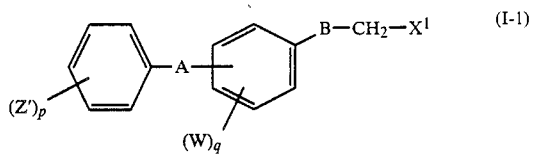

wherein A, B, W, p and q are each as defined above, $X^1$ is either one of the following groups:

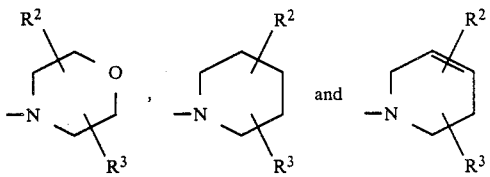

(in which $R^2$ and $R^3$ are each as defined above) and Z' is, the same or different, and is a hydrogen atom, a halogen atom, a lower alkyl group, a lower alkoxy group, a halo(lower)alkyl group, a methylenedioxy group or a halo(lower)alkoxy group is obtainable by reacting a compound of the formula:

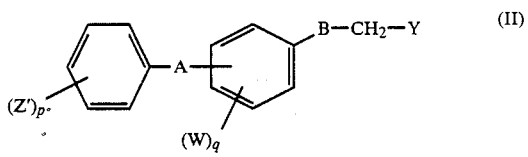

wherein A, B, W, Z', p, and q are each as defined above and Y is a chlorine atom, a bromine atom, an iodine atom or a group of the formula: $-OSO_2B$ in which B is a lower alkyl group or a phenyl group optionally substituted with lower alkyl with a compound of the formula:

$$H-X^1 \qquad (III)$$

wherein $X^1$ is as defined above.

Procedure (2)

A heterocyclic compound of the formula:

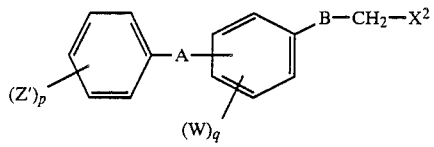

wherein A, B, W, Z′, p and q are each as defined above and $X^2$ is either one of the following groups:

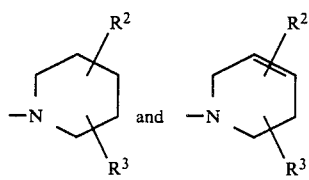

in which $R^2$ and $R^3$ are each as defined above is obtainable by reacting the compound (II) with a pyridine compound of the formula:

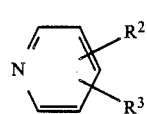

wherein $R^2$ and $R^3$ are each as defined above to give a pyridinium salt of the formula:

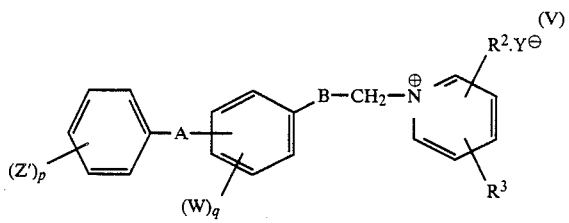

wherein $R^2$, $R^3$, A, B, W, Y, Z′, p, q are each as defined above, followed by reduction.

Procedure (3)

A heterocyclic compound of the formula:

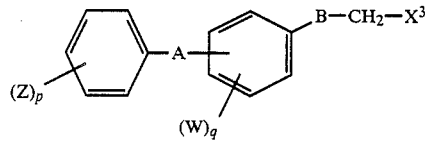

wherein A, B, W, Z, p, q are each as defined above and $X^3$ is either one of the following groups:

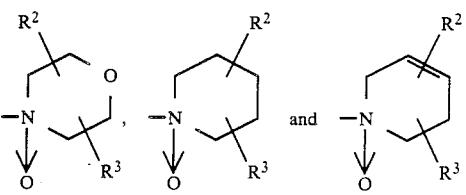

(in which $R^2$ and $R^3$ are each as defined above) is obtainable by subjecting the heterocyclic compound (I-1) to oxidation.

Procedure (4)

A heterocyclic compound of the formula:

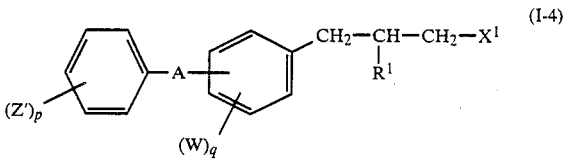

wherein $R^1$, A, W, $X^1$, Z′, p and q are each as defined above obtainable by reacting a compound of the formula:

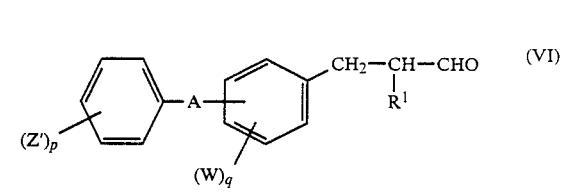

wherein $R^1$, A, W, Z′, p and q are each as defined above with the compound (III) to give a compound of the formula:

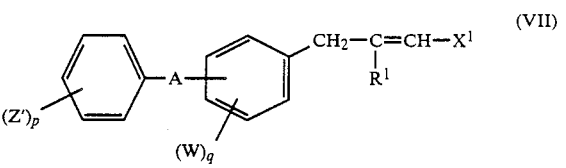

wherein $R^1$, A, W, $X^1$, Z′, p and q are each as defined above, followed by reduction.

Procedure (5)

The heterocyclic compound (I-1) is obtainable by reacting a compound of the formula:

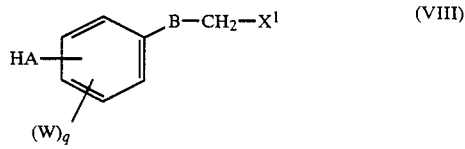

wherein A, B, W, $X^1$ and q are each as defined above with a compound of the formula:

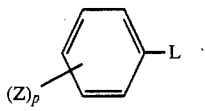

(IX)

wherein Z and p are each as defined above and L is a halogen atom.

Each of the above reactions will be hereinafter explained in more detail.

In Procedure (1), the compound (II) and the compound (III) are reacted usually in a molar proportion of about 1:1-10. The reaction is normally performed at a temperature of about −20° to 200° C. (preferably about 0° to 150° C.) for a period of about 5 minutes to 100 hours (preferably about 5 minutes to 20 hours). The use of an inert solvent is not essential. When used, it may be chosen from ethers (e.g. diethyl ether, tetrahydrofuran, dioxane), alcohols (e.g. ethylene glycol, glycerol, methanol, ethanol), N,N-dimethylacetamide, dimethylsulfoxide, etc. These solvents may be employed alone or in combination.

After completion of the reaction, the reaction mixture is made neutral or basic, extracted, concentrated and, if necessary, subjected to further treatment such as chromatography or distillation to give the objective compound (I-1).

In Procedure (2), the formation of the pyridinium salt (V) in the former step is normally carried out by reacting the compound (II) with the compound (IV) in a molar proportion of about 1:1-10 in the presence or absence of an inert solvent at a temperature of about −20° to 200° C. (preferably about 0° to 170° C.) for a period of about 5 minutes to 100 hours (preferably about 5 minutes to 20 hours). When the inert solvent is used, it may be chosen from alcohols (e.g. ethylene glycol, glycerol, methanol, ethanol), ketones (e.g. acetone, methyl ethyl ketone, methyl isobutyl ketone), N,N-dimethylformamide, N,N-dimethylacetamide, dimethylsulfoxide, etc. These may be used alone or in combination. If desired, the pyridinium salt (V) thus produced may be washed with ethers such as diethyl ether, tetrahydrofuran or dioxane.

The reduction in the latter step may be performed by treatment of the pyridinium salt (V) with a reducing agent under reaction conditions as properly decided depending upon the reducing agent. When the reduction is effected by the use of a metal hydride (e.g. lithium borohydride, sodium borohydride, potassium borohydride) as the reducing agent, there may be used an inert solvent chosen from alcohols (e.g. ethylene glycol, glycerol, methanol, ethanol), ethers (e.g. diethyl ether, tetrahydrofuran, dioxane), esters (e.g. methyl acetate, ethyl acetate), aromatic hydrocarbons (e.g. benzene, toluene), acetic acid, water, etc. These solvents may be used alone or in combination. When the reduction is carried out with an aluminum hydride compound such as lithium aluminum hydride or aluminum diisobutyl hydride, there may be employed an insert solvent chosen from ethers (e.g. diethyl ether, tetrahydrofuran, dioxane), aromatic hydrocarbons (e.g. benzene, toluene), etc. These solvents can be used alone or in combination. In these cases, the reduction is normally accomplished using the reducing agent in an amount of about 1 to 10 moles to one mole of the pyridinium salt (V) at a temperature of about −70° to 200° C. (preferably about −50° to 100° C.) for a period of about 5 minutes to 100 hours (preferably about 5 minutes to 50 hours).

Except the case where at least one of Z' and W in the formula (V) is halogen, the reduction may be carried out by catalytic hydrogenation using a per se conventional hydrogenation catalyst such as platinum or palladium in an amount of trace to 1 mol to one mol of the pyridinium salt (V), normally in an inert solvent chosen from alcohols (e.g. methanol, ethanol), aromatic hydrocarbons (e.g. benzene, toluene), esters (e.g. ethyl acetate), acetic acid, water, etc. at a temperature of about 0° to 200° C. for a period of about 1 to 100 hours.

Upon termination of the reduction, the reaction mixture is made neutral or basic and subjected to an ordinary post-treatment to give the objective compound (I-2).

In Procedure (3), the oxidation is carried out by treatment of the compound (I-1) with an oxidizing agent in an amount of about 1 to 10 mol per mol of the compound (I-1), usually in an inert solvent at a temperature of about −20° to 200° C. (preferably about 0° to 150° C.), for a period of about 5 minutes to 200 hours (preferably about 1 to 100 hours). As the oxidizing agent, there may be used any one chosen from hydrogen peracid, perbenzoic acid, m-chloroperbenzoic acid, peracetic acid, etc. Examples of the solvent are halogenated hydrocarbons (e.g. chloroform, dichloromethane, dichloroethane), ethers (e.g. diethyl ether, tetrahydrofuran, dioxane), alcohols (e.g. ethylene glycol, glycerol, methanol, ethanol), N,N-dimethylformamide, N,N-dimethylacetamide, dimethylsulfoxide, etc. These may be used solely or in combination.

After completion of the reaction, the reaction mixture is subjected to a post-treatment by a per se conventional procedure to give the compound (I-3).

In Procedure (4), the reaction in the former step is effected by treating the compound (VI) with the compound (III) usually in a molar ratio of about 1:0.1-10 at a temperature of about −20° to 300° C. (preferably about 0° to 250° C.) for a period of about 5 minutes to 200 hours (preferably about 30 minutes to 100 hours), if desired, in an inert solvent chosen from aromatic solvents (e.g. benzene, toluene, xylene, chlorobenzene), aliphatic solvents (e.g. pentane, hexane, heptane, petroleum ether), halogenated solvents (e.g. methylene chloride, chloroform, dichloroethane, dibromoethane, tetrachloroethylene), ethers (e.g. diethyl ether, tetrahydrofuran, dioxane), esters (e.g. methyl acetate, ethyl acetate), alcohols (e.g. methanol, ethanol, ethylene glycol, glycerin), etc. In the reaction system, a dehydrating agent as well as a catalyst may be present to accomplish the reaction quickly and smoothly. The dehydrating agent is usually employed in an amount of about 0.001 to 10 parts by weight to one part by weight of the compound (VI), and its examples are molecular sieve, anhydrous sodium sulfate, anhydrous magnesium sulfate, anhydrous calcium chloride, silica gel, alumina, etc. The catalyst is normally employed in an amount of 0.001 to 10 mol per mol of the compound (VI), and its examples are hydrochloric acid, sulfuric acid, acetic acid, nitric acid, p-toluenesulfonic acid, benzenesulfonic acid, methanesulfonic acid, etc.

The reduction in the latter step may be effected by treatment of the compound (VII) with a reducing agent under reaction conditions as properly decided depending upon the reducing agent. When the reduction is carried out by the use of a metal hydride (e.g. lithium borohydride, sodium borohydride, potassium borohydride) as the reducing agent, there may be used an inert solvent chosen from alcohols (e.g. ethylene glycol, glycerol, methanol, ethanol), ethers (e.g. diethyl ether, tetrahydrofuran, dioxane), esters (e.g. methyl acetate, ethyl acetate), aromatic hydrocarbons (e.g. benzene, toluene), acetic acid, water, etc. These solvents may be used along or in combination. When the reduction is carried out with an aluminum hydride compound such as lithium aluminum hydride or aluminum diisobutyl hydride, there may be employed an inert solvent chosen from ethers (e.g. diethyl ether, tetrahydrofuran, dioxane), aromatic hydrocarbons (e.g. benzene, toluene), etc. These solvents can be used alone or in combination. In these cases, the reduction is normally accomplished using the reducing agent in an amount of about 1 to 10 moles to one mole of the compound (VIII) at a temperature of about −70° to 200° C. (preferably about −50° to 100° C.) for a period of about 5 minutes to 100 hours (favorably about 5 minutes to 50 hours).

Except the case in which at least one of Z' and W in the formula (VII) is halogen, the reduction may be carried out by catalytic hydrogenation using a per se conventional hydrogenation catalyst such as platinium or palladium in an amount of trace to 1 mol to one mol of the compound (VII), normally in an inert solvent chosen from alcohols (e.g. methanol, ethanol), aromatic hydrocarbons (e.g. benzene, toluene), esters (e.g. ethyl acetate), acetic acid, water, etc. at a temperature of about 0° to 200° C. for a period of about 1 to 100 hours.

Upon termination of the reduction, the reaction mixture is made neutral or basic and subjected to an ordinary post-treatment to give the objective compound (I-4).

In Procedure (5), the reaction is effected by treatment of the compound (VIII) with the compound (IX) usually in an amount of about 0.1 to 10 mol per mol of the former at a temperature of about 0° to 300° C. (preferably about 50° to 250° C.) for a period of about 5 minutes to 200 hours (especially about 30 minutes to 100 hours), if desired, in an inert solvent such as N,N-dimethylformamide, N,N-dimethylacetamide, dimethylsulfoxide or sulforane. In the reaction system, an acid-eliminating agent as well as a catalytic substance may be present in order to accomplish the reaction quickly and smoothly. The acid-eliminating agent, which may be chosen from lithium hydroxide, sodium hydroxide, potassium hydroxide, sodium carbonate, potassium carbonate, lithium hydride, sodium hydride, potassium hydride, metallic lithium, metallic sodium, metallic potassium, etc., is usually employed in an amount of about 0.1 to 10 mol to one mol of the compound (VIII). The catalytic substance, of which examples are copper and its compounds (e.g. metal copper, copper oxide, cuprous chloride, cupric chloride), may be used in an amount of 0.001 to 10 mol per mol of the compound (VIII).

Upon termination of the reaction, the reaction mixture is post-treated in a per se conventional manner to give the compound (I-1).

The heterocyclic compounds (I) can easily be converted into their salts. For instance, the heterocyclic compound (I) in a free form is treated with an acid such as an inorganic acid (e.g. hydrochloric acid, sulfuric acid, nitric acid) or an organic acid (e.g. formic acid, acetic acid, propionic acid, methanesulfonic acid, benzenesulfonic acid, p-toluenesulfonic acid) in an amount of about 0.1 to 10 mol to one mol of the heterocyclic compound (I), optionally in an inert solvent to give the corresponding acid addition salt, at a temperature of about 0° to 300° C. (preferably about 0° to 100° C.) for a period of about 1 minute to 200 hours (favorably about 5 minutes to 100 hours). Examples of the inert solvent are ethers (e.g. diethyl ether, tetrahydrofuran, dioxane), aromatic solvents (e.g. benzene, toluene, chlorobenzene), halogenated solvents (e.g. chloroform, dichloromethane, tetrachloroethylene), alcohols (e.g. methanol, ethanol), etc.

Upon completion of the reaction, the reaction mixture may be subjected to a post-treatment by a per se conventional procedure.

Practical embodiments for production of the heterocyclic compounds (I) are illustratively shown in the following Examples.

EXAMPLE 1

2,6-Dimethylmorpholine (1.16 g) was added to 3-(m-phenoxyphenyl)-2-methylpropyl p-toluenesulfonate (0.8 g) at room temperature, and the resultant mixture was stirred at 100° C. for 30 minutes. The reaction mixture was made basic with addition of water (100 ml) and 15% aqueous sodium hydroxide solution (10 ml) thereto and extracted with diethyl ether (50 ml×3). The ether extracts were combined together, washed with saturated aqueous sodium chloride solution, dried over magnesium sulfate and concentrated under reduced pressure. The residue was purified by column chromatography to give 4-[3-(m-phenoxyphenyl)-2-methylpropyl]-2,6-dimethylmorpholine (trans-isomer, 0.16 g; cis-isomer, 0.41 g).

EXAMPLE 2

3-Methoxymethylpyridine (1.75 g) was added to 3-(m-phenoxyphenyl)-2-methylpropyl iodide (1.0 g) at room temperature, and the resultant mixture was stirred at 120° C. for 4 hours. The reaction mixture was cooled to room temperature and washed with diethyl ether three times. Methanol (20 ml) was added thereto, and after addition of sodium borohydride (0.21 g) at room temperature, the resultant mixture was stirred at the same temperature for 15 hours. The resultant mixture was admixed with water (200 ml) and 15% aqueous sodium hydroxide solution (20 ml) and extracted with diethyl ether (50 ml×3). The extracts were combined together, washed with saturated aqueous sodium chloride solution, dried over magnesium sulfate and concentrated under reduced pressure. The residue was purified by column chromatography to give N-[3-(m-phenoxyphenyl)-2-methylpropyl]-3-methoxymethyl-1,2,5,6-tetrahydropyridine (0.2 g).

EXAMPLE 3

N-[3-(m-Phenoxyphenyl)-2-methylpropyl]-3-methoxymethyl-1,2,5,6-tetrahydropyridine (0.2 g) was dissolved in ethanol (20 ml), followed by addition of acetic acid (1 ml) thereto. To the resultant mixture, 5% palladium-carbon (0.2 g) was added at room temperature under nitrogen stream, and then hydrogenation was carried out under nitrogen stream. After absorption of hydrogen was completed, the catalyst was removed by filtration, and the filtrate was combined with 15% aqueous sodium hydroxide solution (20 ml) and extracted with diethyl ether. The ether extract was washed with saturated aqueous sodium chloride solution, dried over magnesium sulfate and concentrated under reduced pressure. The residue was purified by column chromatography to give N-[3-(m-phenoxyphenyl)-2-methylpropyl]-3-methoxymethylpiperidine (0.19 g).

EXAMPLE 4

3-(m-Phenoxyphenyl)-2-methylpropyl iodide (1.0 g) was added to 3-methoxymethylpyridine (1.75 g) at room temperature, and the resultant mixture was stirred at 120° C. for 4 hours, cooled to room temperature and washed with diethyl ether three times. The resultant mixture was admixed with methanol (20 ml) and then with acetic acid (2 ml). To the resulting mixture, 5% palladium-carbon (0.5 g) was added at room temperature under nitrogen stream, and then hydrogenation was carried out under nitrogen stream. After absorption of hydrogen was completed, the catalyst was removed by filtration, and the filtrate was combined with 15% aqueous sodium hydroxide solution (50 ml) and extracted with diethyl ether. The ether layer was washed with saturated aqueous sodium chloride solution, dried over magnesium sulfate and concentrated under reduced pressure. The residue was purified by column chromatography to give N-[3-(m-phenoxyphenyl)-2-methylpropyl]-3-methoxymethylpiperidine (0.2 g).

EXAMPLE 5 cis-4-[3-(m-Phenoxyphenyl)-2-methylpropyl]-2,6-dimethylmorpholine (0.5 g) was dissolved in dichloromethane (10 ml), and m-chloroperbenzoic acid (0.26 g) was added thereto, followed by stirring for 24 hours. After further addition of m-chloroperbenzoic acid (0.26 g), the stirring was continued for 24 hours. To the reaction mixture, 15% aqueous sodium hydroxide solution (30 ml) was added, followed by extraction with ethyl acetate (50 ml×3). The extracts were combined together, washed with saturated aqueous sodium chloride solution, dried over magnesium sulfate and concentrated undere reduced pressure. The residue was purified by column chromatography to give cis-4-[3-(m-phenoxyphenyl)-2-methylpropyl]-2,6-dmethylmorpholine N-oxide (0.2 g).

EXAMPLE 6

Dimethylformamide (5 ml) was added to 60% sodium hydride (0.12 g) under nitrogen stream, and a solution of 4-[3-(3-hydroxyphenyl)-2-methylpropyl]-2,6-dimethylmorpholine (0.48 g) in dimethylformamide (5 ml) was added thereto in 30 minutes, followed by stirring at room temperature for 2 hours. To the reaction mixture, p-iodonitrobenzene (0.97 g) and cuprous chloride (0.1 g) were added, and the resultant mixture was heated under reflux for 10 hours. Then, water (100 ml) was added to the reaction mixture, which was filtered through celite. The celite was washed with toluene (200 ml). The toluene layer and the toluene washing were combined together and shaken with 15% aqueous sodium hydroxide solution (30 ml). The toluene layer was separated, washed with saturated aqueous sodium chloride solution, dried over sodium sulfate and concentrated under reduced pressure. The residue was purified by column chromatography to give 4-[3-(3-(4-nitrophenoxy)phenyl)-2-methylpropyl]-2,6-dimethylmorpholine (cis-isomer, 0.27 g).

EXAMPLE 7

3-(m-Phenoxyphenyl)-2-methylpropylaldehyde (1.0 g) was dissolved in methanol (20 ml), followed by addition of 2,6-dimethylmorpholine (2 g) thereto at room temperature. After addition of molecular sieve (4 Å, 5 g) a catalytic amount of hydrogen chloride gas was introduced therein. The resulting mixture was aged at room temperature for 12 hours. The reaction mixture was filtered to remove molecular sieve, and sodium borohydride (0.16 g) was portionwise added thereto at room temperature while stirring, followed by aging at room temperature for 10 hours. The reaction mixture was poured into water (200 ml) and extracted with ethyl acetate (50 ml×3). The extracts were combined together, washed with saturated aqueous sodium chloride solution, dried over magnesium sulfate and concentrated under reduced pressure. The residue was purified by column chromatography to give 4-[3-(m-phenoxyphenyl)-2-methylpropyl]-2,6-dimethylmorpholine (cis-isomer, 0.25 g; trans-isomer, 0.1 g).

EXAMPLE 8

3-(m-Phenoxyphenyl)-2-methyl-2-propenyl bromide (1.0 g) was added to 2,6-dimethylmorpholine (2.0 g) at 0° C. while stirring, followed by aging at the same temperature for 3 hours. Ice water (100 ml) and 15% aqueous sodium hydroxide solution (30 ml) were added to the resultant mixture to make basic, followed by extraction with ethyl acetate (50 ml×3). The extracts were combined together, washed with saturated aqueous sodium chloride solution, dried over magnesium sulfate and concentrated under reduced pressure. The residue was purified by column chromatography to give 4-[3-(m-phenoxyphenyl)-2-methyl-2-propenyl]-2,6-dimethylmorpholine (cis-isomer, 0.3 g).

In the same manner as above, the heterocyclic compounds (I) as shown in Table 1 were obtained.

TABLE 1

$$\text{(Z)}_p\text{-}\underset{}{\underset{(W)_q}{\text{Ar}}}\text{-A-Ar-B-CH}_2\text{-X} \quad \text{(I)}$$

| Compound No. | (Z)ₚ—⟨Ar⟩—A—⟨Ar⟩—(W)q | B | X | Physical constant (Refractive index or M.P. (°C.) |
|---|---|---|---|---|
| 1 | phenyl-O-phenyl (meta) | —CH₂—CH(CH₃)— | 2,6-dimethylmorpholino (cis) | 1.5383 (22.5) |
| 2 | phenyl-O-phenyl (meta) | —CH₂—CH(CH₃)— | 2-methylmorpholino | 1.5444 (22.6) |
| 3 | phenyl-O-phenyl-F | —CH₂—CH(CH₃)— | 2,6-dimethylmorpholino | 1.5304 (22.0) |
| 4 | phenyl-O-phenyl-F | —CH₂—CH(CH₃)— | 2,6-dimethylmorpholino | 1.5302 (22.0) |
| 5 | phenyl-O-phenyl (meta) | —CH₂—CH₂— | 2-methylmorpholino | 1.5421 (22.5) |
| 6 | phenyl-O-phenyl (meta) | —CH₂—CH₂— | 2,6-dimethylmorpholino | 1.5415 (22.5) |

TABLE 1-continued $$\text{(I)}$$

| Compound No. | (structure with (Z)p, A, (W)q) | B | X | Physical constant (Refractive index or M.P. (°C.)) |
|---|---|---|---|---|
| 7 | 3-phenoxyphenyl | —CH₂—CH(CH₃)— | 3-(hydroxymethyl)piperidin-1-yl | 1.5551 (28.2) |
| 8 | 3-phenoxyphenyl | —CH₂—CH(CH₃)— | 3-(ethoxymethyl)piperidin-1-yl | 1.5327 (27.7) |
| 9 | 3-phenoxyphenyl | —CH₂—CH(CH₃)— | 3,5-dimethylpiperidin-1-yl (cis) | 1.5362 (28.0) |
| 10 | 3-phenoxyphenyl | —CH₂—CH(CH₃)— | 3,5-dimethylpiperidin-1-yl (trans) | 1.5430 (28.0) |
| 11 | 3-phenoxyphenyl | —CH₂—CH(CH₃)— | morpholin-4-yl | 1.5600 (27.7) |
| 12 | 3-phenoxyphenyl | —CH₂—CH(CH₃)— | 3-methylpiperidin-1-yl | 1.5472 (27.7) |
| 13 | 3-phenoxyphenyl | —CH₂—CH(CH₃)— | 4-methylpiperidin-1-yl | 1.5450 (27.7) |
| 14 | 3-phenoxyphenyl | —CH₂—CH(CH₃)— | piperidin-1-yl | 1.5492 (27.7) |

TABLE 1-continued $$\text{(Z)}_p\text{-C}_6\text{H}_4\text{-A-C}_6\text{H}_4(\text{W})_q\text{-B-CH}_2\text{-X} \quad (I)$$

| Compound No. | (Z)p–Ph–A–Ph–(W)q | B | X | Physical constant (Refractive index or M.P. (°C.)) |
|---|---|---|---|---|
| 15 | Ph–O–Ph (3-substituted) | —CH₂—CH(CH₃)— | morpholine N-oxide with 2,6-di-CH₃ | 1.5430 (26.9) |
| 16 | Ph–O–Ph (3-substituted) | —CH₂—CH(CH₃)— | 2-methylpiperidin-1-yl | 1.5593 (25.4) |
| 17 | Ph–O–Ph (3-substituted) | —CH₂—CH(CH₃)— | 4-(1-ethoxy-1-methylethyl)-1,2,3,6-tetrahydropyridin-1-yl | 1.5324 (24.5) |
| 18 | Ph–O–Ph (3-substituted) | —CH₂—CH(CH₃)— | 4-(1-methoxy-1-methylethyl)-1,2,3,6-tetrahydropyridin-1-yl | 1.5458 (24.4) |
| 19 | Ph–O–Ph (3-substituted) | —CH₂—CH(CH₃)— | 4-ethoxypiperidin-1-yl | 1.5432 (24.5) |
| 20 | Ph–O–Ph (3-substituted) | —CH₂—CH(CH₃)— | 3-hydroxypiperidin-1-yl | 1.5560 (24.3) |
| 21 | Ph–O–Ph (3-substituted) | —CH₂—CH(CH₃)— | 4-(1-methoxyethyl)-1,2,3,6-tetrahydropyridin-1-yl | 1.5625 (25.1) |

TABLE 1-continued

Structure (I):

(Z)ₚ—[phenyl]—A—[phenyl](W)_q—B—CH₂—X

| Compound No. | [(Z)ₚ-phenyl-A-phenyl-(W)_q structure] | B | X | Physical constant (Refractive index or M.P. (°C.)) |
|---|---|---|---|---|
| 22 | phenyl-O-phenyl (3-position) | —CH₂—CH(CH₃)— | 1,2,5,6-tetrahydropyridin-3-yl with C(CH₃)₂OH substituent | 1.5526 (24.4) |
| 23 | phenyl-O-phenyl (3-position) | —CH₂—CH(CH₃)— | piperidin-3-yl with C(CH₃)₂OH substituent | 1.5364 (25.8) |
| 24 | phenyl-O-phenyl (3-position) | —CH₂—CH(CH₃)— | 1,2,5,6-tetrahydropyridin-3-yl with CH₂OCH₃ substituent | 1.5432 (25.5) |
| 25 | phenyl-O-phenyl (3-position) | —CH₂—CH(CH₃)— | 1,2,5,6-tetrahydropyridin-3-yl with CH₂OC₂H₅ substituent | 1.5336 (26.5) |
| 26 | phenyl-O-phenyl (3-position) | —CH₂—CH(CH₃)— | piperidin-3-yl with CH(CH₃)OCH₃ substituent | 1.5322 (26.6) |
| 27 | phenyl-O-phenyl (3-position) | —CH₂—CH(CH₃)— | 1,2,5,6-tetrahydropyridin-3-yl with CH(CH₃)OH substituent | 1.5556 (25.8) |
| 28 | phenyl-O-phenyl (3-position) | —CH₂—CH(CH₃)— | 1,2,5,6-tetrahydropyridin-3-yl with CH₂OH substituent | 1.5614 (25.2) |

TABLE 1-continued $$\text{(Z)}_p\text{-phenyl-A-phenyl(W)}_q\text{-B-CH}_2\text{-X} \quad (I)$$

| Compound No. | (Z)$_p$-phenyl-A-phenyl-(W)$_q$ | B | X | Physical constant (Refractive index or M.P. (°C.)) |
|---|---|---|---|---|
| 29 | 3-methylphenyl-O-phenyl | —CH$_2$—CH(CH$_3$)— | 3-ethyl-1,2,5,6-tetrahydropyridin-1-yl | 1.5511 (24.5) |
| 30 | 3-methylphenyl-O-phenyl | —CH$_2$—CH(CH$_3$)— | 3-(1-hydroxyethyl)piperidin-1-yl (CH$_3$, OH) | 1.5377 (23.4) |
| 31 | 3-methylphenyl-O-phenyl | —CH$_2$—CH(CH$_3$)— | 3-ethylpiperidin-1-yl | 1.5382 (24.7) |
| 32 | 3-methylphenyl-O-phenyl | —CH$_2$—CH(CH$_3$)— | 3-(methoxymethyl)piperidin-1-yl (CH$_2$OCH$_3$) | 1.5366 (24.5) |
| 33 | 3-methylphenyl-O-phenyl | —CH$_2$—CH(CH$_3$)— | 3-ethoxypiperidin-1-yl (OC$_2$H$_5$) | 1.5399 (21.9) |
| 34 | 3-methylphenyl-O-phenyl | —CH$_2$—CH(CH$_3$)— | 3-(1-ethoxyethyl)-1,2,5,6-tetrahydropyridin-1-yl (CH$_3$, OC$_2$H$_5$) | 1.5385 (25.0) |
| 35 | 4-chlorophenyl-O-3-methylphenyl | —CH$_2$—CH(CH$_3$)— | cis-2,6-dimethylmorpholin-4-yl (CH$_3$, O, CH$_3$) | 1.5463 (21.0) |

TABLE 1-continued

| Compound No. | (Z)p (W)q | B | X | Physical constant (Refractive index or M.P. (°C.)) |
|---|---|---|---|---|
| 36 | 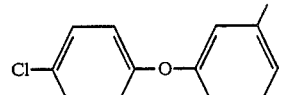 4-Cl-phenoxy-3-methylphenyl | —CH₂—CH(CH₃)— | 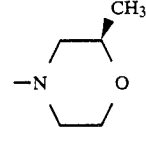 2,6-dimethylmorpholino | 1.5498 (21.0) |
| 37 | 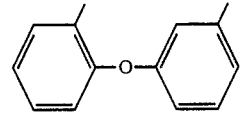 2-Cl-phenoxy-3-methylphenyl | —CH₂—CH(CH₃)— | 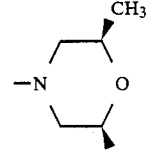 2,6-dimethylmorpholino | 1.5467 (21.6) |
| 38 | 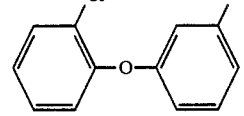 2-Cl-phenoxy-3-methylphenyl | —CH₂—CH(CH₃)— | 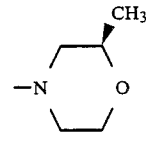 2-methylmorpholino | 1.5480 (20.8) |
| 39 | 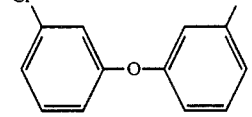 3-Cl-phenoxy-3-methylphenyl | —CH₂—CH(CH₃)— | 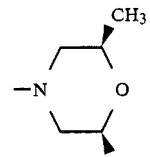 2,6-dimethylmorpholino | 1.5445 (23.3) |
| 40 | 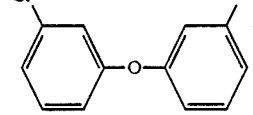 4-Cl-phenoxy-3-methylphenyl | —CH₂—CH(CH₃)— | 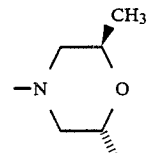 2,6-dimethylmorpholino | 1.5568 (22.0) |
| 41 | 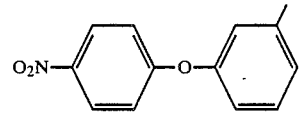 4-NO₂-phenoxy-3-methylphenyl | —CH₂—CH(CH₃)— | 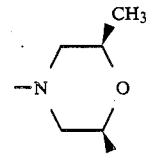 2,6-dimethylmorpholino | 1.5661 (22.5) |

TABLE 1-continued

| Compound No. | (Z)p / (W)q | B | X | Physical constant (Refractive index or M.P. (°C.) |
|---|---|---|---|---|
| 42 | 3,5-difluorophenoxy-phenyl | —CH₂—CH(CH₃)— | cis-2,6-dimethylmorpholino | 1.5172 (21.5) |
| 43 | 3,5-difluorophenoxy-phenyl | —CH₂—CH(CH₃)— | trans-2,6-dimethylmorpholino | 1.5228 (20.5) |
| 44 | 4-cyanophenoxy-phenyl | —CH₂—CH(CH₃)— | cis-2,6-dimethylmorpholino | 1.5561 (22.5) |
| 45 | 3-methylphenoxy-phenyl | —CH₂—CH(CH₃)— | cis-2,6-dimethylmorpholino | 1.5481 (21.5) |
| 46 | 3-methylphenoxy-phenyl | —CH₂—CH(CH₃)— | cis-2,6-dimethylmorpholino | 1.5369 (23.4) |
| 47 | 4-methylphenoxy-phenyl | —CH₂—CH(CH₃)— | cis-2,6-dimethylmorpholino | 1.5366 (23.1) |

TABLE 1-continued

| Compound No. | (Z)p / (W)q structure | B | X | Physical constant (Refractive index or M.P. (°C.)) |
|---|---|---|---|---|
| 48 | H₃C–C₆H₄–O–C₆H₄– | —CH₂—CH(CH₃)— | cis-2,6-dimethylmorpholino | 1.5379 (23.5) |
| 49 | 2-OCH₃–C₆H₄–O–C₆H₄– (meta) | —CH₂—CH(CH₃)— | cis-2,6-dimethylmorpholino | 1.5431 (21.1) |
| 50 | 2-OCH₃–C₆H₄–O–C₆H₄– (meta) | —CH₂—CH(CH₃)— | trans-2,6-dimethylmorpholino | 1.5393 (23.1) |
| 51 | 4-CH₃O–C₆H₄–O–C₆H₄– (meta) | —CH₂—CH(CH₃)— | cis-2,6-dimethylmorpholino | 1.5419 (20.3) |
| 52 | 2-Cl-4-CF₃–C₆H₃–O–C₆H₄– (meta) | —CH₂—CH(CH₃)— | trans-2,6-dimethylmorpholino | 1.5120 (20.4) |
| 53 | 4-CH₃O–C₆H₄–O–C₆H₄– (meta) | —CH₂—CH(CH₃)— | trans-2,6-dimethylmorpholino | 1.5432 (20.5) |

TABLE 1-continued $$\text{(I)}$$

Structure (I): Ar-A-Ar'-B-CH₂-X with (Z)_p on first ring and (W)_q on second ring.

| Compound No. | (Z)_p / (W)_q (aryl-A-aryl substitution) | B | X | Physical constant (Refractive index or M.P. (°C.)) |
|---|---|---|---|---|
| 54 | 2-Cl, 4-F₃C-phenyl–O–(3-methylphenyl) | —CH₂—CH(CH₃)— | cis-2,6-dimethylmorpholino | 1.5131 (21.8) |
| 55 | 2-CH₃-phenyl–O–(3-methylphenyl) | —CH₂—CH(CH₃)— | cis-2,6-dimethylmorpholino | 1.5380 (22.1) |
| 56 | 2-CH₃-phenyl–O–(3-methylphenyl) | —CH₂—CH(CH₃)— | trans-2,6-dimethylmorpholino | 1.5462 (19.6) |
| 57 | 3-CH₃O-phenyl–O–(3-methylphenyl) | —CH₂—CH(CH₃)— | cis-2,6-dimethylmorpholino | 1.5396 (20.6) |
| 58 | 3-CH₃O-phenyl–O–(3-methylphenyl) | —CH₂—CH(CH₃) | 2,6-dimethylmorpholino | 1.5448 (20.9) |
| 59 | 2-F-phenyl–O–(3-methylphenyl) | —CH₂—CH(CH₃)— | cis-2,6-dimethylmorpholino | 1.5258 (20.5) |

TABLE 1-continued

Structure (I): (Z)p-phenyl-A-phenyl(W)q-B-CH2-X

| Compound No. | (Z)p / (W)q aryl group | B | X | Physical constant (Refractive index or M.P. (°C.)) |
|---|---|---|---|---|
| 60 | 2-F-phenyl-O-(3-methylphenyl) | —CH₂—CH(CH₃)— | morpholine with 2,6-di-CH₃ | 1.5265 (20.5) |
| 61 | 3-F-phenyl-O-(3-methylphenyl) | —CH₂—CH(CH₃)— | morpholine with 2,6-di-CH₃ | 1.5351 (20.6) |
| 62 | 3-F-phenyl-O-(3-methylphenyl) | —CH₂—CH(CH₃)— | morpholine with 2,6-di-CH₃ | 1.5367 (19.7) |
| 63 | 4-F-phenyl-O-(3-methylphenyl) | —CH₂—CH(CH₃)— | morpholine with 2,6-di-CH₃ | 1.5295 (20.4) |
| 64 | 4-F-phenyl-O-(3-methylphenyl) | —CH₂—CH(CH₃)— | morpholine with 2,6-di-CH₃ | 1.5303 (20.4) |
| 65 | 3,5-di-Cl-phenyl-O-(3-methylphenyl) | —CH₂—CH(CH₃)— | morpholine with 2,6-di-CH₃ | 1.5516 (20.7) |

TABLE 1-continued $$\underset{(Z)_p}{\phantom{x}}\text{Structure (I)}$$

| Compound No. | (Z)_p / (W)_q (structure) | B | X | Physical constant (Refractive index or M.P. (°C.)) |
|---|---|---|---|---|
| 66 | 3,5-dichlorophenyl–O–(3-methylphenyl) | —CH₂—CH(CH₃)— | 2,6-dimethylmorpholino (cis) | 1.5529 (18.9) |
| 67 | 3,4-dichlorophenyl–O–(3-methylphenyl) | —CH₂—CH(CH₃)— | 2,6-dimethylmorpholino | 1.5520 (20.6) |
| 68 | 3,4-dichlorophenyl–O–(3-methylphenyl) | —CH₂—CH(CH₃)— | 2,6-dimethylmorpholino | 1.5509 (21.3) |
| 69 | 3,5-dimethylphenyl–O–(3-methylphenyl) | —CH₂—CH(CH₃)— | 2,6-dimethylmorpholino | 1.5374 (21.4) |
| 70 | 3,5-dimethylphenyl–O–(3-methylphenyl) | —CH₂—CH(CH₃)— | 2,6-dimethylmorpholino | 1.5400 (22.3) |
| 71 | 2,4-dimethylphenyl–O–(3-methylphenyl) | —CH₂—CH(CH₃)— | 2,6-dimethylmorpholino | 1.5358 (21.0) |

TABLE 1-continued

Structure (I): Diaryl ether with (Z)_p, A, (W)_q, B—CH₂—X

| Compound No. | (Z)_p / (W)_q aryl structure | B | X | Physical constant (Refractive index or M.P. (°C.)) |
|---|---|---|---|---|
| 72 | 2-methyl-4-methylphenyl ether linked to 3-methylphenyl (H₃C-, CH₃ on one ring; other ring methyl) | —CH₂—CH(CH₃)— | 2,6-dimethylmorpholino (—N with CH₃ on both α-carbons, O) | 1.5451 (21.0) |
| 73 | 2,6-dimethyl-4-methylphenyl ether linked to 3-methylphenyl | —CH₂—CH(CH₃)— | 2,6-dimethylmorpholino | 1.5321 (22.0) |
| 74 | 4-tert-butylphenyl ether linked to 3-methylphenyl | —CH₂—CH(CH₃)— | 2,6-dimethylmorpholino | 1.5278 (24.5) |
| 75 | 3-bromophenyl ether linked to 3-methylphenyl | —CH₂—CH(CH₃)— | 2,6-dimethylmorpholino | 1.55565 (21.4) |
| 76 | 2,6-dimethyl-4-methylphenyl ether linked to 3-methylphenyl | —CH₂—CH(CH₃)— | 2,6-dimethylmorpholino | 1.5358 (21.5) |
| 77 | 4-ethylphenyl (H₅C₂—) ether linked to 3-methylphenyl | —CH₂—CH(CH₃)— | 2,6-dimethylmorpholino | 1.5342 (21.4) |

TABLE 1-continued $$\text{(I)}$$

| Compound No. | (Z)p — A — (W)q (aryl groups) | B | X | Physical constant (Refractive index or M.P. (°C.)) |
|---|---|---|---|---|
| 78 | H₅C₂—C₆H₄—O—C₆H₄— (3-methyl) | —CH₂—CH(CH₃)— | cis-2,6-dimethylmorpholino | 1.5360 (21.0) |
| 79 | 2,4,5-trichloro-C₆H₂—O—C₆H₄— (3-methyl) | —CH₂—CH(CH₃)— | cis-2,6-dimethylmorpholino | 1.5571 (22.0) |
| 80 | 2,4,5-trifluoro-C₆H₂—O—C₆H₄— (3-methyl) | —CH₂—CH(CH₃)— | cis-2,6-dimethylmorpholino | 1.5158 (20.6) |
| 81 | 3,4-methylenedioxy (ethylenedioxy)-C₆H₃—O—C₆H₄— (3-methyl) | —CH₂—CH(CH₃)— | cis-2,6-dimethylmorpholino | 1.5487 (22.5) |
| 82 | 3,4-ethylenedioxy-C₆H₃—O—C₆H₄— (3-methyl) | —CH₂—CH(CH₃)— | cis-2,6-dimethylmorpholino | 1.5455 (22.4) |
| 83 | 4-Br—C₆H₄—O—C₆H₄— (3-methyl) | —CH₂—CH(CH₃)— | cis-2,6-dimethylmorpholino | 1.5542 (21.0) |

TABLE 1-continued

| Compound No. | (Z)p / (W)q aryl group | B | X | Physical constant (Refractive index or M.P. (°C.)) |
|---|---|---|---|---|
| 84 | 4-Br-phenyl-O-(3-methylphenyl) | —CH$_2$—CH(CH$_3$)— | 2,6-dimethylmorpholino | 1.5534 (21.7) |
| 85 | 4-F$_3$C-phenyl-O-(3-methylphenyl) | —CH$_2$—CH(CH$_3$)— | 2,6-dimethylmorpholino | 1.5091 (22.3) |
| 86 | 4-F$_3$C-phenyl-O-(phenyl) | —CH$_2$—CH(CH$_3$)— | 2,6-dimethylmorpholino | 1.5166 (20.2) |
| 87 | 3-F$_3$C-phenyl-O-(3-methylphenyl) | —CH$_2$—CH(CH$_3$)— | 2,6-dimethylmorpholino | 1.5065 (23.1) |
| 88 | 3-F$_3$C-phenyl-O-(3-methylphenyl) | —CH$_2$—CH(CH$_3$)— | 2,6-dimethylmorpholino | 1.5069 (20.5) |
| 89 | 2-CN-4-F$_3$C-phenyl-O-(3-methylphenyl) | —CH$_2$—CH(CH$_3$)— | 2,6-dimethylmorpholino | 1.5153 (21.4) |

TABLE 1-continued

Structure (I):

Ar1–A–Ar2–B–CH2–X where Ar1 bears (Z)p and Ar2 bears (W)q.

| Compound No. | Ar1-A-Ar2 (with (Z)p, (W)q) | B | X | Physical constant (Refractive index or M.P. (°C.)) |
|---|---|---|---|---|
| 90 | 2-(m-tolyloxy)-5-(trifluoromethyl)benzonitrile moiety: phenyl with CN (ortho) and CF3 (para to O), linked via O to m-tolyl | —CH2—CH(CH3)— | cis-2,6-dimethylmorpholino (—N with ring containing O, two CH3 groups) | 1.5178 (20.8) |
| 91 | pentafluorophenyl–O–m-tolyl | —CH2—CH(CH3)— | cis-2,6-dimethylmorpholino | 1.4982 (18.7) |
| 92 | 2,3,5,6-tetrafluorophenyl–O–m-tolyl | —CH2—CH(CH3)— | cis-2,6-dimethylmorpholino | 1.4974 (20.3) |
| 93 | 4-(CHF2–CF2O–)phenyl–O–m-tolyl | —CH2—CH(CH3)— | cis-2,6-dimethylmorpholino | 1.5008 (19.5) |
| 94 | 2,4-difluorophenyl–O–m-tolyl | —CH2—CH(CH3)— | cis-2,6-dimethylmorpholino | 1.5242 (20.3) |
| 95 | 2,4-difluorophenyl–O–m-tolyl | —CH2—CH(CH3)— | cis-2,6-dimethylmorpholino | 1.5322 (19.6) |

TABLE 1-continued $$(I)$$

Structural formula (I): Ar-A-Ar'-B-CH₂-X with (Z)ₚ on first ring and (W)_q on second ring.

| Compound No. | (Z)ₚ / (W)_q Aryl group | B | X | Physical constant (Refractive index or M.P. (°C.)) |
|---|---|---|---|---|
| 96 | 2,4,6-trifluorophenoxy-phenyl (F, F, F substituents) | —CH₂—CH(CH₃)— | cis-2,6-dimethylmorpholino | 1.5138 (24.5) |
| 97 | 4-fluoro-3-methylphenoxy-phenyl | —CH₂—CH(CH₃)— | cis-2,6-dimethylmorpholino | 1.5312 (24.5) |
| 98 | 4-fluoro-2-methylphenoxy-phenyl | —CH₂—CH(CH₃)— | cis-2,6-dimethylmorpholino | — |
| 99 | 2-fluorophenoxy-phenyl | —CH₂—CH(CH₃)— | 3,5-dimethylpiperidino | 1.5270 (22.3) |
| 100 | 2-fluorophenoxy-phenyl | —CH₂—CH(CH₃)— | morpholino | 1.5388 (22.7) |
| 101 | 2-fluorophenoxy-phenyl | —CH₂—CH(CH₃)— | piperidino | 1.5442 (19.5) |

TABLE 1-continued $$\text{(Z)}_p - \text{C}_6\text{H}_4 - A - \text{C}_6\text{H}_4(\text{W})_q - B - CH_2 - X \quad (I)$$

| Compound No. | (Z)p—C6H4—A—C6H4—(W)q | B | X | Physical constant (Refractive index or M.P. (°C.)) |
|---|---|---|---|---|
| 102 | phenyl-O-(2-chloro-5-yl)phenyl | —CH₂—CH(CH₃)— | cis-2,6-dimethylmorpholino | 1.5468 (22.5) |
| 103 | phenyl-O-(2-chloro-5-yl)phenyl | —CH₂—CH(CH₃)— | trans-2,6-dimethylmorpholino | 1.5534 (22.0) |
| 104 | 4-fluorophenyl-O-(2-chloro-5-yl)phenyl | —CH₂—CH(CH₃)— | trans-2,6-dimethylmorpholino | 1.5321 (26.0) |
| 105 | 4-chlorophenyl-O-(2-chloro-5-yl)phenyl | —CH₂—CH(CH₃)— | trans-2,6-dimethylmorpholino | 1.5489 (25.0) |
| 106 | 4-chlorophenyl-O-(4-chloro-3-yl)phenyl | —CH₂—CH(CH₃)— | trans-2,6-dimethylmorpholino | — |
| 107 | 4-chlorophenyl-O-(2-fluoro-5-yl)phenyl | —CH₂—CH(CH₃)— | trans-2,6-dimethylmorpholino | 1.5349 (25.2) |

TABLE 1-continued (I)

| Compound No. | (Z)p (W)q | B | X | Physical constant (Refractive index or M.P. (°C.)) |
|---|---|---|---|---|
| 108 | 4-F-phenoxy, 2-F substituted phenyl | —CH₂—CH(CH₃)— | cis-2,6-dimethylmorpholino | 1.5196 (25.2) |
| 109 | 4-Cl-phenoxy, 2-CH₃ substituted phenyl | —CH₂—CH(CH₃)— | cis-2,6-dimethylmorpholino | |
| 110 | phenoxy, 2-OCH₃ substituted phenyl | —CH₂—CH(CH₃)— | cis-2,6-dimethylmorpholino | 1.5421 (25.2) |
| 111 | 4-Cl-phenoxy, 2-OCH₃ substituted phenyl | —CH₂—CH(CH₃)— | cis-2,6-dimethylmorpholino | 1.5409 (25.2) |
| 112 | 4-Cl-phenoxy phenyl | —CH₂—CH(CH₃)— | morpholino | 1.5545 (23.2) |
| 113 | 4-Cl-phenoxy phenyl | —CH₂—CH(CH₃)— | piperidino | 1.5595 (22.0) |
| 114 | 3,5-bis(CF₃)-phenoxy phenyl | —CH₂—CH(CH₃)— | 2-methylmorpholino | 1.4838 (23.5) |

TABLE 1-continued $$\underset{(Z)_p}{\phantom{xxx}}\text{Ar}-A-\text{Ar}-B-CH_2-X \quad (I)$$

| Compound No. | (Z)p–Ar–A–Ar–(W)q | B | X | Physical constant (Refractive index or M.P. (°C.) |
|---|---|---|---|---|
| 115 | phenyl–O–(3-methylphenyl) | —CH=C(CH₃)— | —N(morpholine with 2,6-diCH₃) | 1.5610 (22.5) |
| 116 | 4-Cl-phenyl–O–(3-methylphenyl) | —CH=C(CH₃)— | —N(morpholine with 2,6-diCH₃) | 1.5678 (25.2) |
| 117 | 4-F-phenyl–O–(3-methylphenyl) | —CH=C(CH₃)— | —N(morpholine with 2,6-diCH₃) | 1.5508 (25.2) |
| 118 | 4-Cl-phenyl–O–(3-methylphenyl) | —CH₂—CH(CH₃)— | —N(morpholine with 2,6-diCH₃) (cis, 90%; trans, 10%) | 1.5470 (20.4) |
| 119 | 4-Cl-phenyl–O–(3-methylphenyl) | —CH₂—CH(CH₃)— | —N(morpholine with 2,6-diCH₃) (cis, 70%; trans, 30%) | 1.5462 (20.4) |
| 120 | 4-Cl-phenyl–O–(3-methylphenyl) | —CH₂—CH(CH₃)— | —N(morpholine with 2,6-diCH₃) (cis, 50%; trans, 50%) | 1.5468 (20.5) |

TABLE 1-continued

Structure (I): Ar—A—Ar'—B—CH₂—X, where Ar bears (Z)ₚ and Ar' bears (W)_q

| Compound No. | (Z)ₚ / (W)_q (aromatic portion) | B | X | Physical constant (Refractive index or M.P. (°C.)) |
|---|---|---|---|---|
| 121 | 4-Cl-C₆H₄-O-(3-CH₃-C₆H₄)- | —CH₂—CH(CH₃)— | 2,6-dimethylmorpholin-4-yl (cis, 30%; trans, 70%) | 1.5474 (20.5) |
| 122 | C₆H₅-O-C₆H₄- | —CH₂—CH(CH₃)— | (2S,6S)-2,6-dimethylmorpholin-4-yl | 1.5352 (25.7) |
| 123 | C₆H₅-O-C₆H₄- | —CH₂—CH(CH₃)— | (2R,6S)-2,6-dimethylmorpholin-4-yl | 1.5390 (25.7) |
| 124 | 2-Cl-4-CF₃-C₆H₃-O-C₆H₄- | —CH₂—CH(CH₃)— | 2,6-dimethylmorpholin-4-yl | 1.5097 (23.5) |
| 125 | 2-Cl-4-CF₃-C₆H₃-O-C₆H₄- | —CH₂—CH(CH₃)— | piperidin-1-yl | 1.5191 (23.5) |
| 126 | 2-Cl-4-CF₃-C₆H₃-O-C₆H₄- | —CH₂—CH(CH₃)— | 3-methylpiperidin-1-yl | 1.5176 (23.5) |
| 127 | 2-Cl-C₆H₄-O-C₆H₄- | —CH₂—CH(CH₃)— | piperidin-1-yl | 1.5580 (27.0) |

TABLE 1-continued $$\text{(Z)}_p\text{-}\underset{(W)_q}{\text{Ar-A-Ar}}\text{-B-CH}_2\text{-X} \quad (I)$$

| Compound No. | (Z)p / (W)q structure | B | X | Physical constant (Refractive index or M.P. (°C.) |
|---|---|---|---|---|
| 128 | 4-Cl-C6H4-O-(2-Cl)C6H3- | —CH₂—CH(CH₃)— | —N(morpholine with 2,6-diCH₃) | 1.5523 (23.0) |
| 129 | 4-F-C6H4-O-(2-F)C6H3- | —CH₂—CH(CH₃)— | —N(morpholine with 2,6-diCH₃) | 1.5279 (22.9) |
| 130 | (2-Cl)C6H4-O-C6H4- | —CH₂—CH(CH₃)— | —N(3-methylpiperidine) | 1.5528 (27.0) |
| 131 | (2-Cl)C6H4-O-(2-Cl)C6H3- | —CH₂—CH(CH₃)— | —N(3-methylpiperidine) | 1.5554 (25.0) |
| 132 | (2-Cl)C6H4-O-(2-Cl)C6H3- | —CH₂—CH(CH₃)— | —N(2-methylmorpholine) | 1.5480 (26.0) |
| 133 | (3-Cl)C6H4-O-C6H4- | —CH₂—CH(CH₃)— | —N(2,6-dimethylmorpholine) | 1.5397 (22.5) |
| 134 | (4-Cl)C6H4-O-C6H4- | —CH₂—CH(CH₃)— | —N(2,6-dimethylmorpholine) | 1.5460 (27.5) |

TABLE 1-continued

Structure (I):

$(Z)_p$—[phenyl]—A—[phenyl]($(W)_q$)—B—CH$_2$—X

| Compound No. | $(Z)_p$—[phenyl]—A—[phenyl]—($(W)_q$) | B | X | Physical constant (Refractive index or M.P. (°C.)) |
|---|---|---|---|---|
| 135 | 3,5-difluorophenyl—O—phenyl— | —CH$_2$—CH(CH$_3$)— | (2,6-dimethylmorpholino) cis-2,6-dimethyl —N(CH$_3$)(O)(CH$_3$) | 1.5212 (20.5) |
| 136 | 3-methylphenyl—O—phenyl— | —CH$_2$—CH(CH$_3$)— | cis-2,6-dimethylmorpholino | 1.5391 (19.5) |
| 137 | 4-methylphenyl—O—phenyl— | —CH$_2$—CH(CH$_3$)— | cis-2,6-dimethylmorpholino | 1.5390 (20.5) |
| 138 | 4-(trifluoromethyl)phenyl—O—phenyl— | —CH$_2$—CH(CH$_3$)— | cis-2,6-dimethylmorpholino | 1.5111 (18.3) |
| 139 | 4-fluorophenyl—O—phenyl— | —CH$_2$—CH(CH$_3$)— | morpholino | 1.5435 (27.0) |
| 140 | 4-fluorophenyl—O—phenyl— | —CH$_2$—CH(CH$_3$)— | piperidino | |
| 141 | 4-fluoro-3-methylphenyl—O—phenyl— | —CH$_2$—CH(CH$_3$)— | cis-2,6-dimethylmorpholino | 1.5283 (25.3) |

TABLE 1-continued $$\text{(I)}$$

| Compound No. | (Z)$_p$ ─⟨phenyl⟩─A─⟨phenyl⟩─ (W)$_q$ | B | X | Physical constant (Refractive index or M.P. (°C.)) |
|---|---|---|---|---|
| 142 | 4-(CF$_2$O·CF$_2$H)-phenyl-O-phenyl- | —CH$_2$—CH(CH$_3$)— | (2S,6R)-2,6-dimethylmorpholin-4-yl | 1.5016 (22.0) |
| 143 | 3-(F$_3$C)-phenyl-O-phenyl- | —CH$_2$—CH(CH$_3$)— | 2,6-dimethylmorpholin-4-yl | 1.5075 (24.5) |
| 144 | 4-F-phenyl-O-phenyl- | —CH$_2$—CH(CH$_3$)— | 2,6-dimethylmorpholin-4-yl | 1.5329 (19.7) |
| 145 | 3-F-phenyl-O-phenyl- | —CH$_2$—CH(CH$_3$)— | 2,6-dimethylmorpholin-4-yl | 1.5298 (25.0) |
| 146 | 3,5-di-F-phenyl-O-phenyl- | —CH$_2$—CH(CH$_3$)— | 2,6-dimethylmorpholin-4-yl | 1.5212 (20.5) |
| 147 | 2,4,6-tri-F-phenyl-O-phenyl- | —CH$_2$—CH(CH$_3$)— | 2,6-dimethylmorpholin-4-yl | 1.5131 (24.5) |

TABLE 1-continued $$\text{(Z)}_p \text{—} \underset{\text{(W)}_q}{\text{A}} \text{—} \text{B—CH}_2\text{—X} \quad (I)$$

| Compound No. | (Z)p / (W)q structure | B | X | Physical constant (Refractive index or M.P. (°C.) |
|---|---|---|---|---|
| 148 | 4-Cl-phenyl-O-(2-CH₃)phenyl- | —CH₂—CH(CH₃)— | 2,6-dimethylmorpholino | 1.5390 (27.0) |
| 149 | phenyl-O-phenyl- | —CH=C(CH₃)— | 2,6-dimethylmorpholino | 1.5610 (22.5) |
| 150 | 4-Cl-phenyl-O-phenyl- | —CH=C(CH₃)— | 2,6-dimethylmorpholino | 1.5678 (25.2) |
| 151 | phenyl-S-phenyl- | —CH₂—CH(CH₃)— | 2,6-dimethylmorpholino | 1.5767 (25.4) |
| 152 | 4-Cl-phenyl-S-phenyl- | —CH₂—CH(CH₃)— | 2,6-dimethylmorpholino | |
| 153 | 4-F-phenyl-S-phenyl- | —CH₂—CH(CH₃)— | 2,6-dimethylmorpholino | |

TABLE 1-continued $$\underset{(Z)_p}{\text{Ar}} - A - \underset{(W)_q}{\text{Ar}} - B - CH_2 - X \quad (I)$$

| Compound No. | (Z)p—Ar—A—Ar—(W)q | B | X | Physical constant (Refractive index or M.P. (°C.)) |
|---|---|---|---|---|
| 154 | 4-F₃C-C₆H₄-S-C₆H₄- (meta) | —CH₂—CH(CH₃)— | —N(CH(CH₃)CH₂)₂O (cis-2,6-dimethylmorpholino) | |
| 155 | C₆H₅-S-C₆H₄- (para) | —CH₂—CH(CH₃)— | —N(CH(CH₃)CH₂)₂O | |
| 156 | 4-Cl-C₆H₄-S-C₆H₄- (para) | —CH₂—CH(CH₃)— | —N(CH(CH₃)CH₂)₂O | |
| 157 | 4-F-C₆H₄-S-C₆H₄- (para) | —CH₂—CH(CH₃)— | —N(CH(CH₃)CH₂)₂O | |
| 158 | C₆H₅-O-C₆H₄- (meta) | —CH₂—CH(CH₃)— | —N(CH(CH₃)CH₂)₂O · HCl | 1.5276 (25.2) |
| 159 | C₆H₅-O-C₆H₄- (meta) | —CH₂—CH(CH₃)— | —N(CH(CH₃)CH₂)₂O · (H₂SO₄)½ | |

TABLE 1-continued $$\text{(I)} \quad (Z)_p\text{-C}_6\text{H}_4\text{-A-C}_6\text{H}_4(\text{W})_q\text{-B-CH}_2\text{-X}$$

| Compound No. | $(Z)_p$-Ar-A-Ar-$(W)_q$ | B | X | Physical constant (Refractive index or M.P. (°C.)) |
|---|---|---|---|---|
| 160 | 4-Cl-C₆H₄-O-(3-methylphenyl)- | $-CH_2-CH(CH_3)-$ | $-N[CH(CH_3)CH_2]_2O$ · (HNO₃) | M.P. 151–152° C. |
| 161 | 4-Cl-C₆H₄-O-(3-methylphenyl)- | $-CH_2-CH(CH_3)-$ | $-N[CH(CH_3)CH_2]_2O$ · (HCO₂H) | |
| 162 | 4-Cl-C₆H₄-O-(3-methylphenyl)- | $-CH_2-CH(CH_3)-$ | $-N[CH(CH_3)CH_2]_2O$ · (H₃C-C₆H₄-SO₃H) | M.P. 106–107° C. |
| 163 | 4-Cl-C₆H₄-O-(3-methylphenyl)- | $-CH_2-CH(CH_3)-$ | $-N[CH(CH_3)CH_2]_2O$ · (HCl) | |
| 164 | 4-F-C₆H₄-O-(4-methylphenyl)- | $-CH_2-CH(CH_3)-$ | $-N[CH(CH_3)CH_2]_2O$ · (CH₃CO₂H) | |
| 165 | C₆H₅-S-(3-methylphenyl)- | $-CH_2-CH(CH_3)-$ | $-N[CH(CH_3)CH_2]_2O$ · (HCl) | |

The starting materials in Procedures (1) to (4) can be prepared as shown in the following schemes (a) to (c) wherein $R^1$, $R^2$, $R^3$, A, B, W, $X^1$, Y, Z, p and q are each as defined above and the reagent of the the formula: $Ph_3P=C(R_1)CO_2C_2H_5$ may be replaced by $(C_2H_5O)-PO=C(R_1)CO_2C_2H_5$ or $Zn/BrCH(R_1)CO_2C_2H_5$:

Scheme (a)
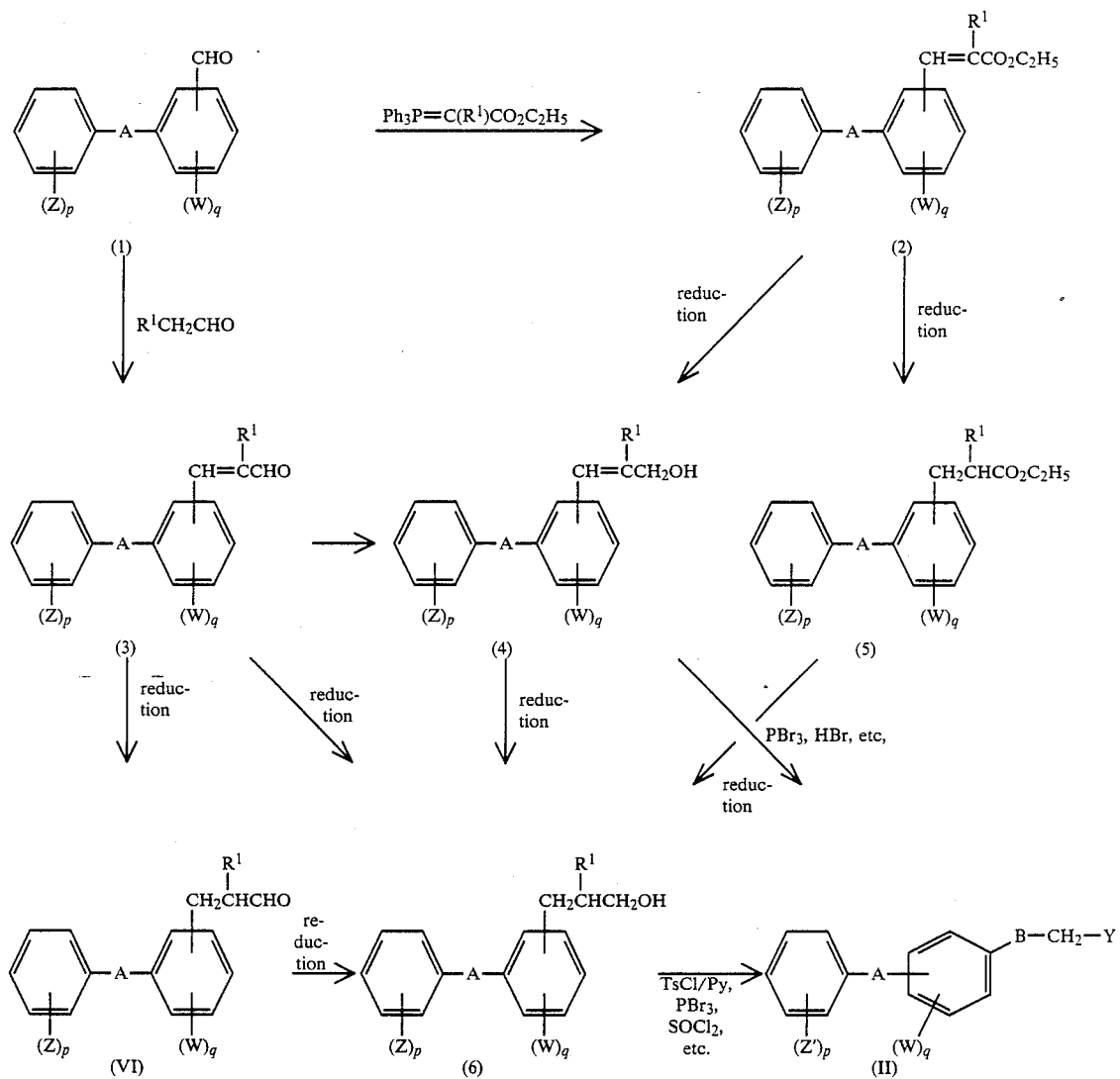
Scheme (b)
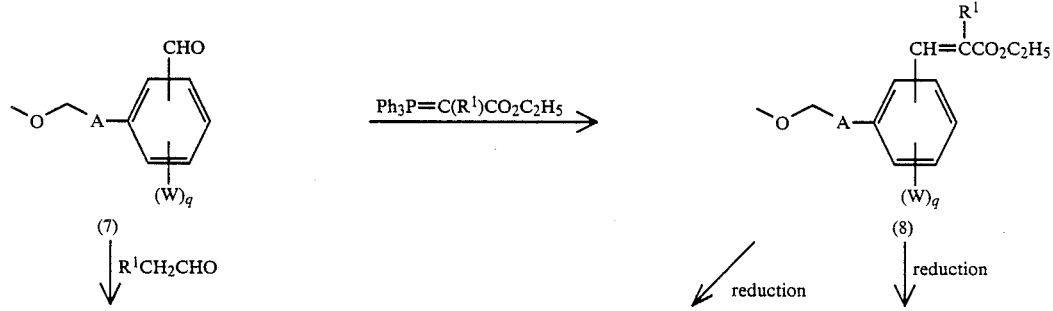

4,837,236
Scheme (b)
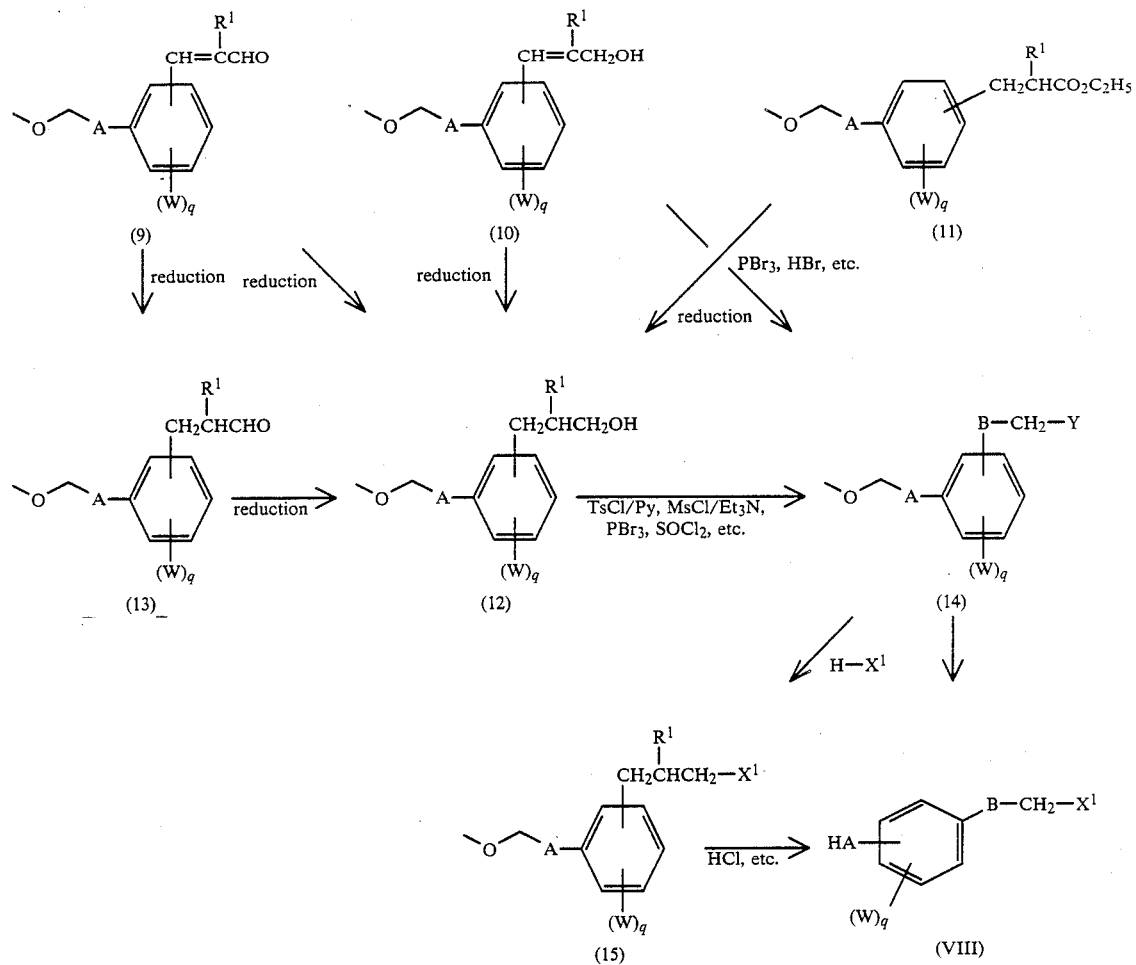
Scheme (c)
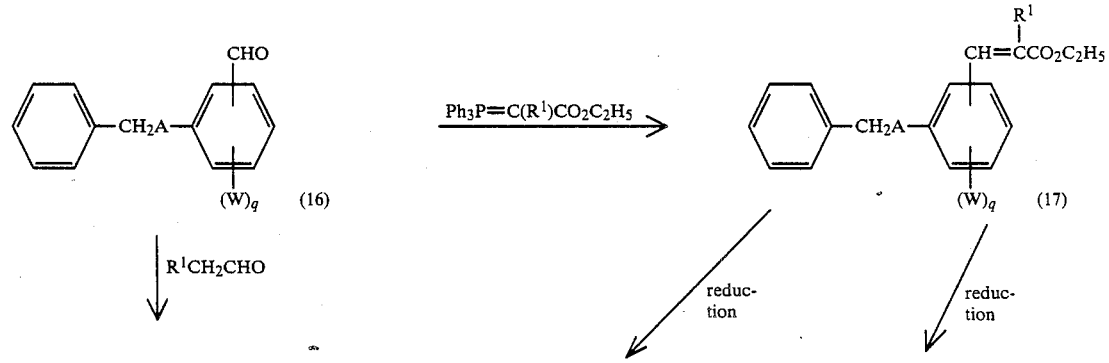

-continued
Scheme (c)

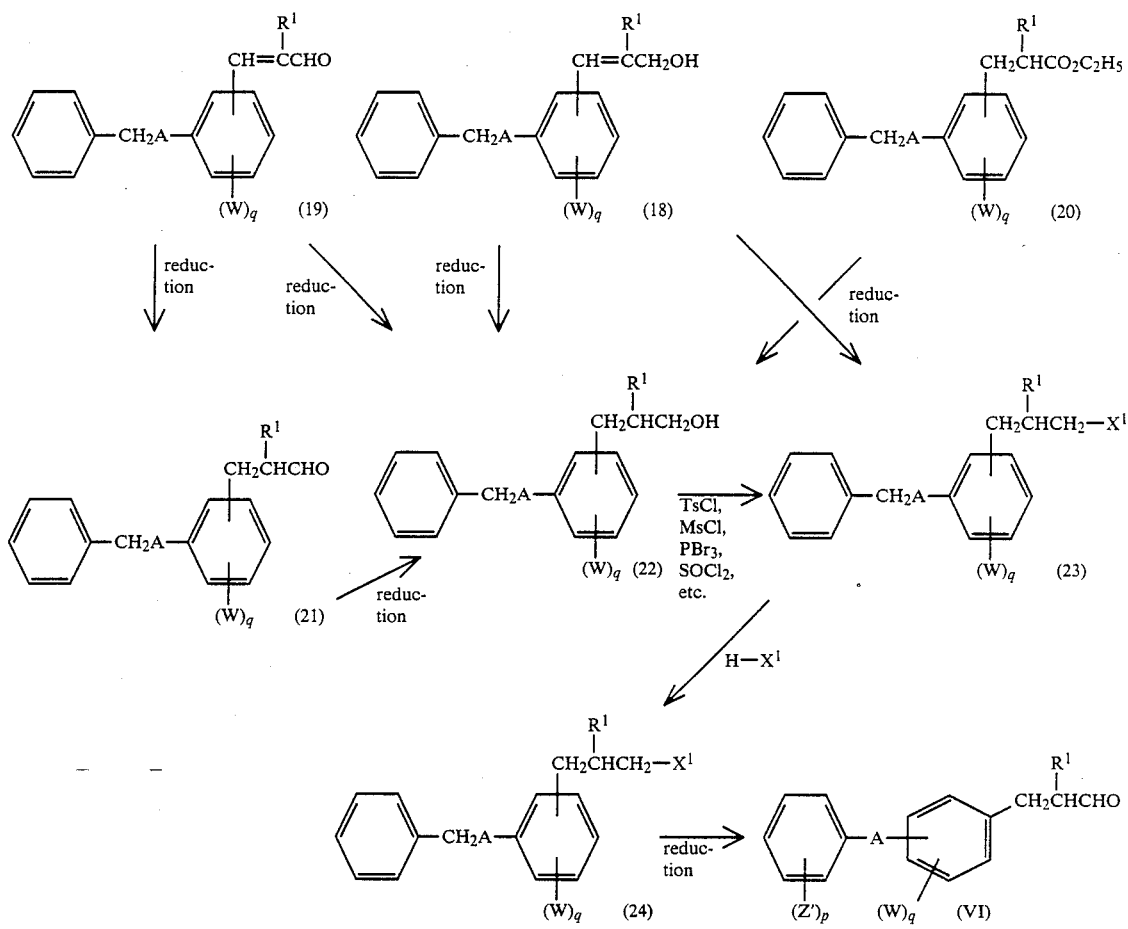

The above reaction scheme (a), (b) and (c) are explained further in detail below.

Scheme (a)

(i) The reaction of the compound (1) with the reagent of the formula: $Ph_3P=C(R^1)CO_2C_2H_5$ is usually carried out in the presence of a base, of which examples are lithium hydride, sodium hydride, potassium hydride, etc., at a temperature of $-20°$ to $300°$ C. (preferably $-10°$ to $100°$ C.) for a period of 5 minutes to 200 hours (preferably 30 minutes to 50 hours). The reagent and the base are respectively used in amounts of 0.1 to 10 mol and of 0.1 to 1.5 mol to one mole of the compound (1). The use of an inert solvent is not essential, but when used, it may be chosen from N,N-dimethylformamide, dimethylsulfoxide, sulforane, aromatic solvents (e.g. benzene, toluene, xylene, chlorobenzene), ethers (e.g. diethyl ether, tetrahydrofuran, dioxane), etc. Upon termination of the reaction, the reaction mixture may be post-treated in a per se conventional manner to give the compound (2).

(ii) The reaction of the compound (1) with the aldehyde of the formula: $R_1CH_2CHO$ is normally carried out in the presence of a base, if necessary, in the existence of a catalyst. Examples of the base are alkali metal hydroxides (e.g. lithium hydroxide, sodium hydroxide, potassium hydroxide), alkaline earth metal hydroxides (e.g. calcium hydroxide), metal alkoxides (e.g. sodium methoxide, sodium ethoxide, potassium methoxide, potassium ethoxide), metal hydrides (e.g. sodium hydride, potassium hydride), etc. As the catalyst, there may be used ammonium salts (e.g. tetrabutylammonium bromide, trimethylbenzylammonium chloride), pyridinium salts (e.g. 1-laurylpyridinium chloride), cyclic ethers (e.g. 18-crown-6), etc. The reaction is normally achieved at a temperature of $-20°$ to $300°$ C. (preferably $0°$ to $100°$ C.) for a period of 5 minutes to 200 hours (favorably 30 minutes to 50 hours). The amounts of the aldehyde, the base and the catalyst are respectively 0.1 to 10 mol, of 0.001 to 1 mol and of 0.001 to 1 mol to one mol of the compound (1). The use of an inert solvent is not essential, but when used, it may be chosen from alcohols (e.g. methanol, ethanol, isopropanol, ethylene glycol, gylcerol), halogenated compounds (e.g. methylene chloride, chloroform, dichloroethane, tetrachloroethane), aromatic compounds (e.g. benzene, toluene, xylene, chlorobenzene), aliphatic compound (e.g. pentane, hexane, heptane, petroleum ether), ethers (e.g. diethyl ether, tetrahydrofuran, dioxane), esters (e.g. methyl acetate, ethyl acetate), amides (e.g. N,N-dimethylformamide, dimethylacetamide), dimethylsulfoxide, sulforane, water, etc. Upon termination of the reaction, the reaction mixture may be post-treated in a per se conventional manner to give the compound (3).

(iii) Reduction of the compound (3) with a reducing agent affords the compound (4). Examples of the reducing agent are alkali metal borohydrides (e.g. lithium hydride, sodium borohydride, potassium borohydride), aluminum hydride compounds (e.g. lithium aluminum hydride), etc. Normally, the reduction is carried out at a temperature of −70° C. to 200° C. (preferably −30° to 100° C.) for a period of 5 mintes to 200 hours (favorably 30 minutes to 50 hours). The amount of the reducing agent is usually from 0.1 to 1 mol to one mol of the compound (3). Further, the reduction is usually carried out in an inert solvent. In the case of an alkali metal borohydride being used as the reducing agent, the solvent may be chosen from alcohols (e.g. methanol, ethanol, ethylene glycol, glycerol), water, etc. In the case of an aluminium hydride compound being used as the reducing agent, the solvent may be selected from ethers (e.g. diethyl ether, tetrahydrofuran, dioxane), etc. Post-treatment of the reaction mixture may be carried out in a per se conventional manner to give the compound (4).

(iv) Reduction of the compound (2) to the compound (5) is usually accomplished by catalytic reduction in the presence of a catalyst (e.g. platinium, palladium, Raney nickel) in an inert solvent at a temperature of 0° to 300° C. for a period of 1 to 200 hours. When desired, potassium acetate or the like may be present in the reaction system. The catalyst and the potassium acetate or the like may be respectively used in amounts of trace to 1 mol and of trace to 10 mol to one mol of the compound (2). Examples of the solvent are alcohols (e.g. methanol, ethanol), aromatic hydrocarbons (e.g. benzene, toluene), esters (e.g. ethyl acetate), acetic acid, water, etc. These may be used solely or in combination. Upon termination of the reaction, the reaction mixture may be post-treated in a per se conventional manner to give the compound (5).

(v) Reduction of the compound (3) to the compound (VI) may be accomplished in the same manner as in (iv).

(vi) Reduction of the compound (VI) to the compound (6) is achieved by the use of a reducing agent such as sodium borohydride, potassium borohydride, lithium aluminium hydride or diisobutyl aluminium hydride, etc., usually in an inert solvent at a temperature of −20° to 200° C. for a period of 5 minutes to 300 hours. The amount of the reducing agent may be from 0.1 to 10 mol to one mol of the compound (VI). When lithium borohydride, sodium borohydride or potassium borohydride is used as the reducing agent, any solvent chosen from alcohols (e.g. methanol, ethanol) or thier mixtures may be used as the reaction medium. When lithium aluminium hydride or diisobutyl aluminium hydride is used, a solvent chosen from ethers (e.g. diethyl ether, tetrahydrofuran, dioxane) or their mixtures is usable as the reaction medium. The reaction mixture is, upon termination of the reaction, post-treated in a per se conventional manner to give the compound (6).

(vii) Reduction of the compound (3) or the compound (4) to the compound (6) may be performed either by the use of a reducing agent or by catalytic reduction. In the former case, lithium aluminium hydride is usable as the reducing agent, and the reaction is usually effected in an inert solvent at a temperature of −20° to 200° C. for a period of 5 minutes to 200 hours. The amount of the reducing agent may be 0.1 to 10 mol to one mol of the compound (3) or (4). Examples of the solvent are ethers (e.g. diethyl ether, tetrahydrofuran, dioxane), etc. In the latter case, a catalyst such as platinium, palladium or Raney nickel is usable, and the reaction is normally effected in an inert solvent at a temperature of 0° to 300° C. for a period of 1 to 200 hours. The catalyst may be used in an amount of trace to 1 mol to one mol of the compound (3) or (4). Examples of the solvent are alcohols (e.g. methanol, ethanol), aromatic hydrocarbons (e.g. benzene, toluene), esters (e.g. ethyl acetate), acetic acid, water and their mixtures. The reaction mixture is, upon termination of the reaction, post-treated in a per se conventional manner to give the compound (6).

(viii) Reduction of the compound (5) to the compound (6) is effected using a reducing agent such as lithium aluminium hydride or diisobutyl aluminium hydride. The reaction is normally effected at a temperature of −20° to 200° C. for a period of 5 to 200 hours in an inert solvent. The amount of the reducing agent may be from 0.1 to 10 mol to 1 mol of the compound (5). Examples of the solvent are ethers (e.g. diethyl ether, tetrahydrofuran, dioxane). Upon termination of the reaction, the reaction mixture may be post-treated in a per se conventinal manner to give the compound (6).

(ix) Reaction of the compound (4) with a halogenating agent gives the compound (II: Y=halogen). The halogenating agent may be chosen from phosphorus compounds (e.g. phosphorus tribromide), sulfur compounds (e.g. thionyl chloride), hydrochloric acid, hydrobromic acid, hydroiodic acid, etc. These may be used solely or in combination. In general, the amount of the halogenating agent is from 0.1 to 50 mol to one mol of the compound (4). The reaction is usually carried out in an inert solvent at a temperature of −10° to 200° C. for a period of 5 minutes to 200 hours. Examples of the solvent are alcohols (e.g. methanol, ethanol), aliphatic hydrocarbons (e.g. pentane, hexane, heptane, petroleum ethers), halogenated compounds (e.g. methylene chloride, chloroform, dichloroethane), aromatic hydrocarbons (e.g. benzene, toluene, chlorobenzene), etc.; these may be used solely or in combination. If necessary, there may be present any additive chosen from amides (e.g. dimethylformamide, dimethylacetamide), amines (e.g. triethylamine), pyridines (e.g. pyridine, 4-aminopyridine), etc. to the reaction system. These additives may be employed in a catalytic amount to 1 mol to one mol of the compound (4). The reaction mixture is, upon termination of the reaction, post-treated in a per se conventinal manner to give the compound (II: Y=halogen).

(x) Reaction of the compound (6) with a halogenating agent gives the compound (II:Y=halogen). The reaction can be achieved in substantially the same manner as in (ix).

(xi) Reaction of the compound (6) with a sulfonylating agent gives the compound (II: Y=sulfonic ester residue). The sulfonylating agent is normally used in an amount of 0.1 to 2 mol to one mole of the compound (6). Examples of the sulfonylating agent are methanesulfonyl chloride, ethanesulfonyl chloride, benzenesulfonyl chloride, p-toluenesulfonyl chloride, etc. The reaction is usually carried out in an inert solvent at a temperature of −50° to 100° C. for a period of 5 minutes to 200 hours. Examples of the solvent are ethers (e.g. diethyl ether, tetrahydrofuran, dioxane), halogenated compounds (e.g. methylene chloride, chloroform, dichloroethane, tetrachloroethylene), pyridines, etc. If necessary, a base may be incorporated into the reaction system. Examples of the base are tertiary amines (e.g. triethylamine), pyridines, etc. These may be used in an amount of 0.1 to 10 mol to one mol of the compound (6). The reaction mixture is, upon termination of the reaction, post-treated in a per se conventinal manner to give the compound (II: Y=sulfonic ester residue).

The starting compound (1) is obtainable, for instance, by the method as described in JP-A-61443/1973.

Scheme (b)

(i) The reaction of the compound (7) with a compound of the formula: Ph$_3$P=C(R$^1$)CO$_2$C$_2$H$_5$ to give the compound (8) is carried out in the same manner as in (i) in Scheme (a).

(ii) The reaction of the compound (7) with a compound of the formula: R$^1$CH$_2$CHO to give the compound (9) is carried out in the same manner as in (ii) in Scheme (a).

(iii) The reduction of the compound (9) to give the compound (10) is carried out in the same manner as in (iii) in Scheme (a).

(iv) The reduction of the compound (8) to give the compound (11) is carried out in the same manner as in (iv) in Scheme (a).

(v) The reduction of the compound (9) to give the compound (13) is carried out in the same manner as in (v) in Scheme (a).

(vi) The reduction of the compound (9) or the compound (10) to give the compound (12) is carried out in the same manner as in (vii) in Scheme (a).

(vii) The halogenation of the compound (12) to give the compound (14) is carried out in the same manner as in (x) in Scheme (a).

(viii) The reduction of the compound (13) to give the compound (12) is carried out in the same manner as in (vi) in Scheme (a).

(ix) The reduction of the compound (11) to give the compound (12) is carried out in the same manner as in (viii) in Scheme (a).

(x) Reaction of the compound (14) with a compound of the formula: HX$^1$ to give the compound (15) is usually effected in an inert solvent at a temperature of −20° to 200° C. for a period of 5 minutes to 200 hours. The amount of the compound HX$^1$ may be from 0.1 to 200 mol to one mol of the compound (14). As the solvent, there may be exemplified amides (e.g. dimethylformamide, dimethylacetamide), sulfur compunds (e.g. dimethylsulfoxide, sulphorane), alcohols (e.g. methanol, ethanol), aromatic compounds (e.g. benzene, toluene, xylene, chlorobenzene), halogenated compounds (e.g. methylene chloride, chloroform, dichloroethane, tetrachloroethylene), ethers (e.g. diethyl ether, tetrahydrofuran, dioxane), water and their mixtures. When desired, a base may be incorporated into the reaction system, normally in an amount of 0.1 to 2 mol to to one mol of the compound (14). Examples of the base are alkali metal hydroxides (e.g. lithium hydroxide, sodium hydroxide, potassium hydroxide), carbonates (e.g. sodium carbonate, potassium carbonate), metal hydrides (e.g. lithium hydride, sodium hydride, potassium hydride), tertiary amines (e.g. triethylamine), etc. The reaction mixture is, upon termination of the reaction, post-treated in any conventional manner to give the compound (15).

(xi) Treatment of the compound (15) with an acid to the compound (VIII) may be carried out, for instance, in an inert solvent at a temperature of −20° to 200° C. for a period of 5 minutes to 300 hours. As the acid, there may be employed chloric acid, hydrobromic acid, hydroidic acid, sulfuric acid, perchloric acid, methanesulfonic acid, benzenesulfonic acid, p-toluenesulfonic acid, etc. These acids may be used in an amount is 0.1 to 10 mol to one mol of the compound (15). Examples of the solvent are alcohols (e.g. methanol, ethanol), water and their mixtures. The reaction mixture is, upon termination of the reaction, post-treated in any conventional manner to give the compound (VIII).

The starting compound (7) is obtainable, for instance, by treating chloromethyl methyl ether with m-hydroxybenzaldehyde or p-hydroxybenzaldehyde.

Scheme (c)

All the reactions in this scheme can be accomplished in substantially the same manner as in scheme (a).

The starting compound (16) is obtainable, for instance, by reacting benzyl bromide with m-hydroxybenzaldehyde or p-hydroxybenzaldehyde.

Practical embodiments for preparation of the intermediary compounds in the scheme (a) to (c) are illustratively shown in the following Reference Examples.

REFERENCE EXAMPLE 1

3-Phenoxybenzaldehyde (55 g) was dissolved in methanol (300 ml), followed by the addition of potassium hydroxide (0.78 g). The resultant mixture was heated to 40° to 45° C., and propionaldehyde (48.6 g) was dropwise added thereto in 2 hours while stirring, followed by aging at the same temperature for 2 hours. The reaction mixture was poured into ice-water (1.5 liters) and extracted with ethyl acetate (300 ml×3), combined, washed with a saturated aqueous sodium chloride and concentrated under reduced pressure to give 3-(m-phenoxyphenyl)-2-methyl-2-propenylaldehyde (50 g).

REFERENCE EXAMPLE 2

3-(m-Phenoxyphenyl)-2-methyl-2-propenylaldehyde (30 g) was dissolved in ethyl acetate (200 ml), followed by addition of potassium acetate (15 g). 5% Palladium carbon (3 g) was added thereto to effect a catalytic reduction under a hydrogen pressure (1 atm) until absorption of hydrogen ceased. Then, the reaction system was replaced by nitrogen, and the reaction mixture was filtered by celite and concentrated under reduced pressure to give 3-(m-phenoxyphenyl)-2-methylpropylaldehyde (25 g).

REFERENCE EXAMPLE 3

A solution of lithium aluminum hydride (2.4 g) in dry tetrahydrofuran (80 ml) was heated under reflux under nitrogen stream, and a solution of 3-(mphenoxyphenyl)-2-methyl-2-propenylaldehyde (10 g) in tetrahydrofuran (20 ml) was dropwise added thereto in 1 hour, followed by aging for 1 hour under reflux. The reaction mixture was cooled to room temperature and poured into ice-water (200 ml) under nitrogen stream, filtered by celite and separated. The aqueous layer was extracted with ethyl acetate (50 ml) and combined with the organic layer, dired over magnesium sulfate and concentrated udner reduced pressure to give 3-(m-phenoxyphenyl)-2-methylpropanol (6 g).

REFERENCE EXAMPLE 4

3-(m-Phenoxyphenyl)-2-methylpropanol (10 g) was dissolved in pyridine (40 ml), followed by p-toluensulfonyl chloride (8.65 g) at a temperature below −5° C. The resultant mixture was aged at 0° C. for 5 hours and water (10 ml) was added thereto at a temperature below 0° C. The reaction mixture was poured into ice-water (200 ml) and extracted with diethyl ether (100 ml×3). The etheral layer was combined and washed with 20% aqueous sulfuric acid (100 ml×2), saturated aqueous sodium hydrogen carbonate (200 ml×2) and a saturated aqueous sodium chloride in order, dried over magnesium sulfate and concentrated under reduced pressure to give 3-(m-phenoxyphenyl)-2-methylpropyl-p-toluenesulfonate (8 g).

REFERENCE EXAMPLE 5

3-(m-Phenoxyphenyl)-2-methyl-2-propenylaldehyde (10 g) was dissolved in methanol (100 ml), followed by gradual addition of sodium borohydride (0.8g) at room temperature. The resultant mixture was aged at room temperature for 5 hours and concentrated under reduced pressure. Water (200 ml) was added to the reaction mixture, which was then extracted with ethyl acetate (100 ml), dried over magnesium sulfate and concentrated under reduced pressure to give 3-(m-phenoxyphenyl)-2-methyl-2-propenyl alcohol (7.5 g).

REFERENCE EXAMPLE 6

A mixture of 47% hydrobromic acid (3.0 g) and phosphorus tribromide (15.7 ml) was stirred at 40° C. for 3 hours, and a solution of 3-(m-phenoxyphenyl)-2-methyl-2-propenyl alcohol (9.5 g) in ethanol (20 ml) was dropwise added thereto at 10° C. The resultant mixture was aged at the same temperature for 5 hours, poured into ice-water (200 ml) and extracted with diethyl ether (100 ml×2). The ethereal layer was combined, washed with a saturated aqueous sodium chloride, dried over magnesium sulfate and concentrated under reduced pressure to give 3-(m-phenoxyphenyl)-2-methyl-propenylbromide (6 g).

REFERENCE EXAMPLE 7

To a suspension of 62% sodium hydride (10.5 g) in N,N-dimethylformamide (100 ml), a solution of m-hydroxybenzaldehyde (30 g) in N,N-dimethylformamide (100 ml) was dropwise added at 0° C. with stirring, and stirring was continued at room temperature for 2 hours. Chloromethyl methyl ether (23.8 g) was dropwise added thereto under ice-cooling. The reaction mixture was aged at room temperature for 2 hours with stirring, poured into ice-water (1.5 liters) and extracted with ethyl acetate (200 ml×2). The ethyl acetate layer was washed with 10% aqueous hydrogen chloride (200 ml×2) and a saturated aqueous sodium chloride in order, dried over magnesium sulfate and concentrated under reduced pressure to give m-methoxymethoxybenzaldehyde (20 g).

REFERENCE EXAMPLE 8

To a solution of m-methoxymethoxybenzaldehyde (10 g) in methanol (100 ml), potassium hydroxide (0.34 g) was added, followed by dropwise addition of propionaldehyde (5.15 g) at 40° to 45° C. in 2 hours with stirring. The reaction mixture was stirred at the same temperature for 2 hours, poured into ice-water (500 ml) and extracted with ethyl acetate (100 ml×3). The ethyl acetate layer was combined, washed with a saturated aqueous sodium chloride and concentrated under reduced pressure to give 3-(m-methoxymethoxyphenyl)-2-methyl-2-propenylaldehyde (9 g).

REFERENCE EXAMPLE 9

A solution of lithium aluminium hydride (2.76 g) in dry tetrahydrofuran (80 ml) was heated under reflux in nitrogen stream, and a solution of 3-(m-methoxymethoxyphenyl)-2-methyl-2-propenylaldehyde (10 g) in tetrahydrofuran (20 ml) was dropwise added thereto in 1 hour. The resultant solution was aged for 1 hour under reflux, cooled to room temperature and poured into ice-water (200 ml) under nitrogen stream. The reaction mixture was filtered by celite and separated. The aqueous layer was extracted with ethyl acetate (50 ml), combined with the organic layer, dried over magnesium sulfate and concentrated under reduced pressure to give 3-(m-methoxymethoxyphenyl)-2-methylpropanol (6.4 g).

REFERENCE EXAMPLE 10

3-(m-Methoxymethoxyphenyl)-2-methylpropanol (10 g) was dissolved in pyridine (40 ml), followed by addition of p-toluenesulfonyl chloride (10.0 g) at a temperature below −5° C. with stirring. The resultant mixture was aged at 0° C. for 5 hours and water (10 ml) was added thereto at a temperature below 0° C. The reaction mixture was poured into ice-water (200 ml) and extracted with diethyl ether (100 ml×3). The ethereal layer was combined, washed with 20% aqueous sulfuric acid (100 ml×2), a saturated aqueous sodium hydrogen carbonate (100 ml×2) and a saturated aqueous sodium chloride in order, dried over magnesium sulfate and concentrated under reduced pressure to give 3-(m-methoxymethoxyphenyl)-2-methylpropyl-p-toluenesulfonate (7.3 g).

REFERENCE EXAMPLE 11

2,6-Dimethylmorpholine (10.0 g) was heated to 100° C. with stirring, and 3-(m-methoxymethoxyphenyl)-2-methylpropyl-p-toluenesulfonate (5.0 g) was dropwise added thereto in 1 hour. The reaction mixture was aged at 100° C. for 2 hours with stirring, cooled to room temperature, and after addition of 15% aqueous sodium hydroxide (50 ml), extracted with diethyl ether (50 ml×3). The organic layer was combined, washed with a saturated aqueous sodium chloride, dried over magnesium sulfate and concentrated under reduced pressure to give 4-[3-(m-methoxymethoxyphenyl)-2-methylpropyl]-2,6-dimethylmorpholine (1.2 g).

REFERENCE EXAMPLE 12

4-[3-(m-Methoxymethoxyphenyl)-2-methylpropyl]-2,6-dimethylmorpholine (1 g) was dissolved in methanol (10 ml), and 36% hydrochloric acid (5 ml) was added thereto in 30 minutes under ice-cooling. The reaction mixture was aged at room temperature for 10 hours, neutralized with a saturated sodium bicarbonate and extracted with ethyl acetate (50 ml×3). The organic layer was combined, washed with a saturated aqueous sodium chloride, dried over magnesium sulfate and concentrated under reduced pressure to give 4-[3-(m-hydroxyphenyl)-2-methylpropyl]-2,6-dimethylmorpholine (0.3 g).

REFERENCE EXAMPLE 13

2,6-Dimethylmorpholine (10.0 g) was added to 3-(m-methoxymethoxyphenyl)-2-methylpropyl-p-toluenesulfonate (5.0 g) at room temperature and allowed to react at 100° C. for 30 minutes while stirring. The reaction mixture was made basic with addition of water (500 ml) and 15% aqueous sodium hydroxide (50 ml), extracted with ethyl acetate (50 ml×3) and combined with the organic layer. The resultant mixture was washed with a saturated aqueous sodium chloride, dried over magnesium sulfate and concentrated under reduced pressure. The reaction mixture thus obtained was dissolved in methanol (20 ml), and after addition of 36% hydrochloric acid (10 ml), stirred at room temperature for 10 hours. The resulting mixture was made neutral with gradual addition of sodium hydrogen carbonate, poured into water (200 ml) and extracted with ethyl acetate (50 ml×3). The organic layer was combined, washed with a saturated aqueous sodium chloride, dried over magnesium sulfate and concentrated under reduced pressure. The residue was purified by column chromatography to give 4-[(m-hydroxyphenyl)-2-methylpropyl]-2,6-dimethylmorpholine (trans-isomer, 0.5 g; cis-isomer, 1.2 g).

In the same manner as above, the compounds as shown in Table 2 were obtained.

TABLE 2

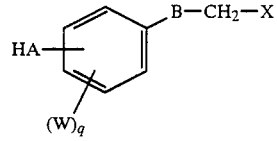

| (W)$_q$ | B | X | Physical constant (Refractive index or M.P. (°C.)) |
|---|---|---|---|
| 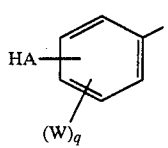 | —CH$_2$—CH(CH$_3$)— | 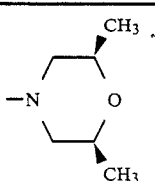 | 1.5238 (26.8) |
| 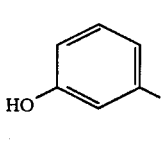 | —CH$_2$—CH(CH$_3$)— | 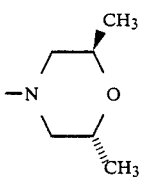 | |
| 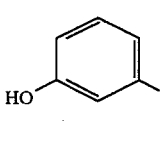 | —CH$_2$—CH(CH$_3$)— | 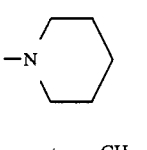 | |
| 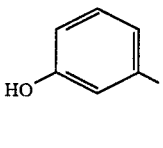 | —CH=C(CH$_3$)— | 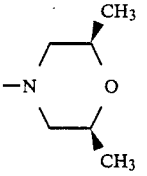 | |
| 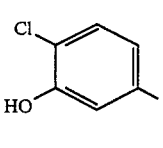 | —CH$_2$—CH(CH$_3$)— | 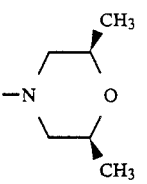 | |
| 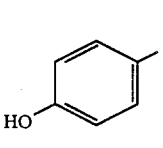 | —CH$_2$—CH(CH$_3$)— | 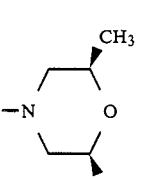 | M.P. 111–112° C. |

TABLE 2-continued

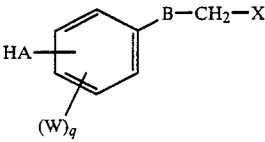

| (W)q | B | X | Physical constant (Refractive index or M.P. (°C.)) |
|---|---|---|---|
| 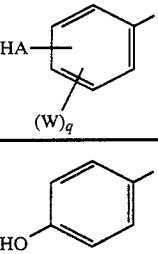 | —CH₂—CH(CH₃)— | 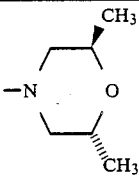 | |
| 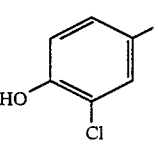 | —CH₂—CH(CH₃)— | 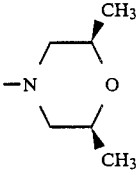 | |
| 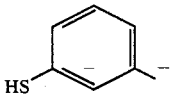 | —CH₂—CH(CH₃)— | 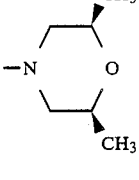 | |
| 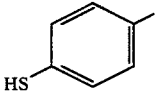 | —CH₂—CH(CH₃)— | 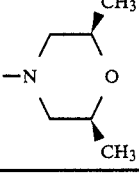 | |

Practical embodiments for preapration of the compound (7) wherein A represents a sulfur atom are illustratively shown in the following Reference Examples.

REFERENCE EXAMPLE 14

To a suspension of 60% sodium hydride (3.5 g) in N,N-dimethylformamide (150 ml), m-bromobenzene thiol (15.0 g) was dropwise added in 1 hour under ice-cooling. The resultant mixture was stirred at room temperature for 2 hours for aging, and chloromethyl methyl ether (7.7 g) was dropwise added thereto in 1 hour under ice-cooling. Aging was continued at room temperature for 2 hours, and the reaction mixture was poured into ice-water (500 ml) and extracted with ethyl acetate (100 ml×3). The organic layer was combined, washed with 1N hydrochloric acid (200 ml×2) and neutralized with a saturated aqueous sodium bicarbonate. The aqueous layer was dried over magnesium sulfate and concentrated under reduced pressure to give methoxymethyl-m-bromophenylthio ether (14.5 g).

REFERENCE EXAMPLE 15

Methoxymethyl-m-bromothio ether (5 g) was dissolved in dry tetrahydrofuran (50 ml) and cooled to a temperature below −60° C., and n-butyl lithium (1.5M solution; 15.5 ml) was dropwise added thereto in 10 minutes under nitrogen stream. The resultant mixture was aged at −50° C. for 1 hour, followed by addition of N,N-dimethylformamide (2.33 g). The reaction mixture was further aged at room temperature overnight and poured into ice-water (100 ml). 1N Hydrochloric acid (1.00 ml) was added to the mixture, which was then extracted with ethyl acetate (50 ml×3). The organic layer was combined, washed with a saturated aqueous sodium bicarbonate, dried over magnesium sulfate and concentrated under reduced pressure. The residue was purified by column chromatography to give m-methoxythiomethoxybenzaldehyde (1.4 g).

Among the heterocyclic compounds (I) of the invention, those having a morpholine ring in which both R² and R³ are not hydrogen atoms have two kinds of geometric isomers (i.e. cis-isomer and trans-isomer) due to steric configuration of R² and R³. This invention covers these isomers and their mixtures, which are usable as fungicides.

In the practical use of the heterocyclic compounds (I) as fungicides, they may be applied as such or in preparation forms such as emulsifiable concentrates, wettable powders, suspensions, powders or granules. Such preparation forms can be formulated in a conventional manner by mixing at least one of the heterocyclic compounds (I) with an appropriate solid or liquid carrier(s) or diluent(s) and, if necessary, an appropriate adjuvant(s) (e.g. surfactants, adherents, dispersants, stabilizers) for improving the dispersibility and other properties of the active ingredient.

Examples of the solid carriers or diluents are fine powders or granules of kaolin clay, attapulgite clay, bentonite, terra alba, pyrophyllite, talc, diatomaceous earth, calcite, corn rachis powders, walnut powders, urea, ammonium sulfate, synthetic hydrated silica, etc. As the liquid carrier or diluent, there may be exemplified aromatic hydrocarbons (e.g. xylene, methylnaphtalene), alcohols (e.g. isopropanol, ethylene glycol, cellosolve), ketones (e.g. acetone, cyclohexanone, isophorone), soybean oil, cotton seed oil, dimethylsulfoxide, acetonitrile, water, etc.

The surface active agent used for emulsification, dispersion or spreading may be any of the anionic and non-ionic type of agents. Examples of the surface active agent include anionic surfactants and non-ionic surfactants such as alkylsulfates, alkylarylsulfonates, dialkylsulfosuccinates, phosphates of polyoxyethylenealkylaryl ethers, condensates of naphthalenesulfonic acid and formalin, polyoxyethylene alkyl ethers, polyoxyethylene polyoxypropylene block copolymers, sorbitan fatty acid esters and polyoxyethylene sorbitan fatty acid esters. Examples of the auxiliary agents include ligninsulfonates, sodium alginate, polyvinyl alcohol, gum arabic, CMC (carboxymethyl cellulose), PAP (isopropyl acid phosphate), etc.

The active ingredient of the heterocyclic compound (I) as the fungicide is generally used in a range of 0.1 to 100 grams, preferably 0.2 to 20 grams, per are. When it is used in the form of the foregoing preparations, the concentration of the active ingredient is generally within a range of 0.001 to 10% by weight, preferably 0.005 to 1% by weight. However, the heterocyclic compound (I) in the form of dusts or granules is normally applied as such without dilution.

It is also notable that the heterocyclic compound (I) may be used as a seed-disinfectant. The heterocyclic compound (I) is also used in admixture with other fungicides to promote their fungicidal activity. Further, for enhancement of their fungicidal potency, they may be applied in association with insecicides, miticides, nematocides, plant-growth regulators, fertilizers, etc.

Some practical embodiments of the fungicidal composition according to the invention are illustratively shown in the following Formulation Examples wherein part(s) are by weight.

FORMULATION EXAMPLE 1

Fifty parts of each of Compound Nos. 1 to 165, 3 parts of calcium ligninsulfonates, 2 parts of sodium laurylsulfonate and 45 parts of synthetic hydrated silica are mixed and thoroughly pulverized to obtain a wettable powder.

FORMULATION EXAMPLE 2

Twenty-five parts of each of Compound Nos. 1 to 165, 3 parts of polyoxyethylene sorbitan monooleate, 3 parts of CMC and 69 parts of water are mixed and thoroughly pulverized until the particle size of the active ingredient becomes less than 5 microns to obtain a suspension.

FORMULATION EXAMPLE 3

Two parts of each of Compound Nos. 1 to 165, 88 parts of kaolin clay and 10 parts of talc are mixed and thoroughly pulverized to obtain powders.

FORMULATION EXAMPLE 4

Twenty parts of each of Compound Nos. 1 to 165, 14 parts of polyoxyethylene styrylphenyl ether, 6 parts of calcium dodecylbenzenesulfonic acid and 60 parts of xylene are mixed together to obtain an emulsifiable concentrate.

FORMULATION EXAMPLE 5

Two parts of each of Compound Nos. 1 to 165, 1 part of synthetic hydrated silica, 2 parts of calcium ligninsulfonate, 30 parts of bentonite and 65 parts of kaolin clay are mixed and thoroughly pulverized with addition of water to obtain granules.

Typical test data indicating the excellent fungicidal activity of the heterocyclic compounds (I) are shown below wherein the controlling effect (e.g., preventive effect and curative effect) was evaluated by visually observing the infectious state, i.e. the degrees of fungal colonies and infected spots on the leaves, stems, etc. of the test plants and classified into the following disease indices:

| Disease index | Percentage of infected area |
|---|---|
| 5 | No infection |
| 4 | Infected area of about 10% |
| 3 | Infected area of about 30% |
| 2 | Infected area of about 50% |
| 1 | Infected area of about 70% |
| 0 | Infected area of above 70% and materially different preventive effect was not exerted in comparison with the non-treated test plant |

The compounds as shown in Table 3 were used for comparison:

TABLE 3

| Compound No. | Structure | Remarks |
|---|---|---|
| A | OHCHN\CH—N(ring)N—CH/NHCHO with $Cl_3C$ and $CCl_3$ substituents | Commercially available fungicide |

TABLE 3-continued

| Compound No. | Structure | Remarks |
|---|---|---|
| B | (dimethylmorpholine)-N-CH$_2$CH$_2$CH$_2$-(CH(CH$_3$))-C$_6$H$_4$-C(CH$_3$)$_3$ | Commercially available fungicide |

TEST EXAMPLE 1

Controlling effect on powdery mildew of wheat (*Erysiphe graminis*)

A plastic pot was filled with sandy soil, and seeds of wheat (var: Nohrin No. 73) were sowed therein and grown in a greenhouse for 10 days until expansion of their second leaves. The test compound formulated in an emulsifiable concentrate according to Formulation Example 4 and diluted with water to a prescribed concetration was thoroughly sprayed over the seedlings of the test plants, and spores of *Erysipha graminis* were inoculated by spreading over the plants, which were further grown at 15° C. in the greenhouse for 10 days and subjected to observation of the preventive effect. Also, the test for curvative effect was conducted as follows: spores of *Erysiphe graminis* were spread over the seedlings just after the expansion of their second leaves; the plants were kept at 15° C. for 2 days and, after treatment with the test compound in the same manner as above, further grown at 15° C. for 6 days and examined. The results are shown in Table 4.

TABLE 4

| Compound No. | Concentration of active ingredient (ppm) | Preventive effect | Curative effect |
|---|---|---|---|
| 1 | 200 | 5 | 5 |
|   | 50 | 5 | 5 |
| 2 | 200 | 5 | 5 |
|   | 50 | 5 | 5 |
| 3 | 200 | 5 | 5 |
|   | 50 | 5 | 5 |
| 4 | 200 | 5 | 5 |
|   | 50 | 5 | 5 |
| 6 | 200 | 5 | 5 |
|   | 50 | 5 | 5 |
| 8 | 200 | 5 | 5 |
|   | 50 | 5 | 5 |
| 9 | 200 | 5 | 5 |
|   | 50 | 5 | 5 |
| 10 | 200 | 5 | 5 |
|   | 50 | 5 | 5 |
| 11 | 200 | 5 | 5 |
|   | 50 | 5 | 5 |
| 12 | 200 | 5 | 5 |
|   | 50 | 5 | 5 |
| 13 | 200 | 5 | 5 |
|   | 50 | 5 | 5 |
| 14 | 200 | 5 | 5 |
|   | 50 | 5 | 5 |
| 15 | 200 | 5 | 5 |
|   | 50 | 5 | 5 |
| 16 | 200 | 5 | 5 |
|   | 50 | 5 | 5 |
| 17 | 200 | 5 | 5 |
|   | 50 | 5 | 5 |
| 18 | 200 | 5 | 5 |
|   | 50 | 5 | 5 |
| 19 | 200 | 5 | 5 |
|   | 50 | 5 | 5 |
| 20 | 200 | 5 | 5 |
|   | 50 | 5 | 5 |
| 21 | 200 | 5 | 5 |
|   | 50 | 5 | 5 |
| 22 | 200 | 5 | 5 |
|   | 50 | 5 | 5 |
| 23 | 200 | 5 | 5 |
|   | 50 | 5 | 5 |
| 24 | 200 | 5 | 5 |
|   | 50 | 5 | 5 |
| 25 | 200 | 5 | 5 |
|   | 50 | 5 | 5 |
| 26 | 200 | 5 | 5 |
|   | 50 | 5 | 5 |
| 29 | 200 | 5 | 5 |
|   | 50 | 5 | 5 |
| 31 | 200 | 5 | 5 |
|   | 50 | 5 | 5 |
| 32 | 200 | 5 | 5 |
|   | 50 | 5 | 5 |
| 33 | 200 | 5 | 5 |
|   | 50 | 5 | 5 |
| 34 | 200 | 5 | 5 |
|   | 50 | 5 | 5 |
| 35 | 200 | 5 | 5 |
|   | 50 | 5 | 5 |
| 36 | 200 | 5 | 5 |
|   | 50 | 5 | 5 |
| 37 | 200 | 5 | 5 |
|   | 50 | 5 | 5 |
| 38 | 200 | 5 | 5 |
|   | 50 | 5 | 5 |
| 39 | 200 | 5 | 5 |
|   | 50 | 5 | 5 |
| 40 | 200 | 5 | 5 |
|   | 50 | 5 | 5 |
| 41 | 200 | 5 | 5 |
|   | 50 | 5 | 5 |
| 42 | 200 | 5 | 5 |
|   | 50 | 5 | 5 |
| 43 | 200 | 5 | 5 |
|   | 50 | 5 | 5 |
| 44 | 200 | 5 | 5 |
|   | 50 | 5 | 5 |
| 45 | 200 | 5 | 5 |
|   | 50 | 5 | 5 |
| 46 | 200 | 5 | 5 |
|   | 50 | 5 | 5 |
| 47 | 200 | 5 | 5 |
|   | 50 | 5 | 5 |
| 48 | 200 | 5 | 5 |
|   | 50 | 5 | 5 |
| 49 | 200 | 5 | 5 |
|   | 50 | 5 | 5 |
| 50 | 200 | 5 | 5 |
|   | 50 | 5 | 5 |
| 51 | 200 | 5 | 5 |
|   | 50 | 5 | 5 |
| 52 | 200 | 5 | 5 |
|   | 50 | 5 | 5 |
| 53 | 200 | 5 | 5 |
|   | 50 | 5 | 5 |
| 54 | 200 | 5 | 5 |
|   | 50 | 5 | 5 |
| 55 | 200 | 5 | 5 |
|   | 50 | 5 | 5 |

TABLE 4-continued

| Compound No. | Concentration of active ingredient (ppm) | Controlling effect | |
|---|---|---|---|
| | | Preventive effect | Curative effect |
| 56 | 200 | 5 | 5 |
| | 50 | 5 | 5 |
| 57 | 200 | 5 | 5 |
| | 50 | 5 | 5 |
| 58 | 200 | 5 | 5 |
| | 50 | 5 | 5 |
| 59 | 200 | 5 | 5 |
| | 50 | 5 | 5 |
| 60 | 200 | 5 | 5 |
| | 50 | 5 | 5 |
| 61 | 200 | 5 | 5 |
| | 50 | 5 | 5 |
| 62 | 200 | 5 | 5 |
| | 50 | 5 | 5 |
| 63 | 200 | 5 | 5 |
| | 50 | 5 | 5 |
| 65 | 200 | 5 | 5 |
| | 50 | 5 | 5 |
| 66 | 200 | 5 | 5 |
| | 50 | 5 | 5 |
| 67 | 200 | 5 | 5 |
| | 50 | 5 | 5 |
| 68 | 200 | 5 | 5 |
| | 50 | 5 | 5 |
| 69 | 200 | 5 | 5 |
| | 50 | 5 | 5 |
| 70 | 200 | 5 | 5 |
| | 50 | 5 | 5 |
| 71 | 200 | 5 | 5 |
| | 50 | 5 | 5 |
| 72 | 200 | 5 | 5 |
| | 50 | 5 | 5 |
| 73 | 200 | 5 | 5 |
| | 50 | 5 | 5 |
| 74 | 200 | 5 | 5 |
| | 50 | 5 | 5 |
| 75 | 200 | 5 | 5 |
| | 50 | 5 | 5 |
| 76 | 200 | 5 | 5 |
| | 50 | 5 | 5 |
| 77 | 200 | 5 | 5 |
| | 50 | 5 | 5 |
| 78 | 200 | 5 | 5 |
| | 50 | 5 | 5 |
| 79 | 200 | 5 | 5 |
| | 50 | 5 | 5 |
| 80 | 200 | 5 | 5 |
| | 50 | 5 | 5 |
| 81 | 200 | 5 | 5 |
| | 50 | 5 | 5 |
| 83 | 200 | 5 | 5 |
| | 50 | 5 | 5 |
| 84 | 200 | 5 | 5 |
| | 50 | 5 | 5 |
| 85 | 200 | 5 | 5 |
| | 50 | 5 | 5 |
| 86 | 200 | 5 | 5 |
| | 50 | 5 | 5 |
| 87 | 200 | 5 | 5 |
| | 50 | 5 | 5 |
| 88 | 200 | 5 | 5 |
| | 50 | 5 | 5 |
| 89 | 200 | 5 | 5 |
| | 50 | 5 | 5 |
| 90 | 200 | 5 | 5 |
| | 50 | 5 | 5 |
| 91 | 200 | 5 | 5 |
| | 50 | 5 | 5 |
| 92 | 200 | 5 | 5 |
| | 50 | 5 | 5 |
| 93 | 200 | 5 | 5 |
| | 50 | 5 | 5 |
| 94 | 200 | 5 | 5 |
| | 50 | 5 | 5 |
| 96 | 200 | 5 | 5 |
| | 50 | 5 | 5 |
| 97 | 200 | 5 | 5 |
| | 50 | 5 | 5 |
| 99 | 200 | 5 | 5 |
| | 50 | 5 | 5 |
| 100 | 200 | 5 | 5 |
| | 50 | 5 | 5 |
| 101 | 200 | 5 | 5 |
| | 50 | 5 | 5 |
| 102 | 200 | 5 | 5 |
| | 50 | 5 | 5 |
| 103 | 200 | 5 | 5 |
| | 50 | 5 | 5 |
| 104 | 200 | 5 | 5 |
| | 50 | 5 | 5 |
| 105 | 200 | 5 | 5 |
| | 50 | 5 | 5 |
| 110 | 200 | 5 | 5 |
| | 50 | 5 | 5 |
| 111 | 200 | 5 | 5 |
| | 50 | 5 | 5 |
| 112 | 200 | 5 | 5 |
| | 50 | 5 | 5 |
| 113 | 200 | 5 | 5 |
| | 50 | 5 | 5 |
| 114 | 200 | 5 | 5 |
| | 50 | 5 | 5 |
| 115 | 200 | 5 | 5 |
| | 50 | 5 | 5 |
| 116 | 200 | 5 | 5 |
| | 50 | 5 | 5 |
| 117 | 200 | 5 | 5 |
| | 50 | 5 | 5 |
| 118 | 200 | 5 | 5 |
| | 50 | 5 | 5 |
| 119 | 200 | 5 | 5 |
| | 50 | 5 | 5 |
| 120 | 200 | 5 | 5 |
| | 50 | 5 | 5 |
| 121 | 200 | 5 | 5 |
| | 50 | 5 | 5 |
| 122 | 200 | 5 | 5 |
| | 50 | 5 | 5 |
| 123 | 200 | 5 | 5 |
| | 50 | 5 | 5 |
| 124 | 200 | 5 | 5 |
| | 50 | 5 | 5 |
| 126 | 200 | 5 | 5 |
| | 50 | 5 | 5 |
| 127 | 200 | 5 | 5 |
| | 50 | 5 | 5 |
| 128 | 200 | 5 | 5 |
| | 50 | 5 | 5 |
| 129 | 200 | 5 | 5 |
| | 50 | 5 | 5 |
| 130 | 200 | 5 | 5 |
| | 50 | 5 | 5 |
| 131 | 200 | 5 | 5 |
| | 50 | 5 | 5 |
| 132 | 200 | 5 | 5 |
| | 50 | 5 | 5 |
| 133 | 200 | 5 | 5 |
| | 50 | 5 | 5 |
| 134 | 200 | 5 | 5 |
| | 50 | 5 | 5 |
| 135 | 200 | 5 | 5 |
| | 50 | 5 | 5 |
| 136 | 200 | 5 | 5 |
| | 50 | 5 | 5 |
| 137 | 200 | 5 | 5 |
| | 50 | 5 | 5 |
| 138 | 200 | 5 | 5 |
| | 50 | 5 | 5 |
| 139 | 200 | 5 | 5 |
| | 50 | 5 | 5 |
| 141 | 200 | 5 | 5 |
| | 50 | 5 | 5 |
| 143 | 200 | 5 | 5 |
| | 50 | 5 | 5 |
| 144 | 200 | 5 | 5 |
| | 50 | 5 | 5 |

TABLE 4-continued

| Compound No. | Concentration of active ingredient (ppm) | Controlling effect Preventive effect | Curative effect |
|---|---|---|---|
| 145 | 200 | 5 | 5 |
|  | 50 | 5 | 5 |
| 146 | 200 | 5 | 5 |
|  | 50 | 5 | 5 |
| 147 | 200 | 5 | 5 |
|  | 50 | 5 | 5 |
| 148 | 200 | 5 | 5 |
|  | 50 | 5 | 5 |
| 149 | 200 | 5 | 5 |
|  | 50 | 5 | 5 |
| 150 | 200 | 5 | 5 |
|  | 50 | 5 | 5 |
| 151 | 200 | 5 | 5 |
|  | 50 | 5 | 5 |
| 158 | 200 | 5 | 5 |
|  | 50 | 5 | 5 |
| 160 | 200 | 5 | 5 |
|  | 50 | 5 | 5 |
| 162 | 200 | 5 | 5 |
|  | 50 | 5 | 5 |
| A | 200 | 4 | 5 |
|  | 50 | 1 | 0 |
| B | 200 | 5 | 5 |
|  | 50 | 5 | 4 |

TEST EXAMPLE 2

Curative effect on leaf spot of wheat (*Septoria tritici*)

A plastic pot was filled with sandy soil, and seeds of wheat (var: Nohrin No. 73) were sowed therein and grown in a greenhouse for 8 days. A spore suspension of *Septoria tritici* was inoculated to the seedlings of the test plants by spraying. The plants were kept at 15° C. under dark and humid conditions for 3 days and grown under illumination for 4 days. The test compound formulated in an emulsifiable concentrate according to Formulation Example 4 and diluted with water to a prescribed concentration was thoroughly sprayed over the plants. The plants were further grown at 15° C. under illumination for 11 days and subjected to observation for the curative effect. The results are shown in Table 5.

TABLE 5

| Compound No. | Concentration of active ingredient (ppm) | Curative effect |
|---|---|---|
| 1 | 200 | 5 |
|  | 50 | 3 |
| 5 | 200 | 5 |
|  | 50 | 3 |
| 11 | 200 | 5 |
|  | 50 | 5 |
| 35 | 200 | 5 |
|  | 50 | 4 |
| 36 | 200 | 5 |
|  | 50 | 5 |
| 37 | 200 | 5 |
|  | 50 | 3 |
| 39 | 200 | 5 |
|  | 50 | 4 |
| 42 | 200 | 5 |
|  | 50 | 5 |
| 44 | 200 | 5 |
|  | 50 | 3 |
| 45 | 200 | 5 |
|  | 50 | 5 |
| 46 | 200 | 5 |
|  | 50 | 5 |
| 47 | 200 | 5 |
|  | 50 | 5 |
| 51 | 200 | 5 |
|  | 50 | 4 |
| 55 | 200 | 5 |
|  | 50 | 5 |
| 56 | 200 | 5 |
|  | 50 | 3 |
| 57 | 200 | 5 |
|  | 50 | 5 |
| 59 | 200 | 5 |
|  | 50 | 5 |
| 60 | 200 | 5 |
|  | 50 | 3 |
| 61 | 200 | 5 |
|  | 50 | 5 |
| 62 | 200 | 5 |
|  | 50 | 5 |
| 63 | 200 | 5 |
|  | 50 | 5 |
| 71 | 200 | 5 |
|  | 50 | 5 |
| 75 | 200 | 5 |
|  | 50 | 4 |
| 81 | 200 | 5 |
|  | 50 | 3 |
| 82 | 200 | 5 |
|  | 50 | 3 |
| 83 | 200 | 5 |
|  | 50 | 3 |
| 100 | 200 | 5 |
|  | 50 | 5 |
| 102 | 200 | 5 |
|  | 50 | 5 |
| 103 | 200 | 5 |
|  | 50 | 3 |
| 110 | 200 | 5 |
|  | 50 | 3 |
| 112 | 200 | 5 |
|  | 50 | 5 |
| 113 | 200 | 5 |
|  | 50 | 3 |
| 115 | 200 | 5 |
|  | 50 | 3 |
| 116 | 200 | 5 |
|  | 50 | 5 |
| 117 | 200 | 5 |
|  | 50 | 5 |
| 118 | 200 | 5 |
|  | 50 | 5 |
| 119 | 200 | 5 |
|  | 50 | 5 |
| 120 | 200 | 5 |
|  | 50 | 5 |
| 122 | 200 | 5 |
|  | 50 | 5 |
| 129 | 200 | 5 |
|  | 50 | 3 |
| 133 | 200 | 5 |
|  | 50 | 3 |
| 141 | 200 | 5 |
|  | 50 | 4 |
| 144 | 200 | 5 |
|  | 50 | 5 |
| 145 | 200 | 5 |
|  | 50 | 4 |
| 151 | 200 | 5 |
|  | 50 | 5 |
| 158 | 200 | 5 |
|  | 50 | 4 |
| 160 | 200 | 5 |
|  | 50 | 4 |
| A | 200 | 0 |
|  | 50 | 0 |
| B | 200 | 0 |
|  | 50 | 0 |

TEST EXAMPLE 3

Preventive effect on eye spot (*Pseudocercosporella herpotrichoides*) of wheat

A plastic pot was filled with sandy soil, and seeds of wheat (var: Nohrin No. 73) were sowed therein and grown in a greenhouse for 10 days. The test compound formulated in a suspension according to Formulation Example 2 and diluted with water to a prescribed concentration was thoroughly sprayed to the seedlings and, after air-drying, a spore suspension of *Pseudocercosporella herpotrichoides* was inoculated thereto by spraying. The plants were kept at 15° C. under dark and humid conditions for 4 days, further grown under illuminated and humid conditions for 4 days and subjected to observation for the preventive effect. The results are shown in Table 6.

TABLE 6

| Compound No. | Concentration of active ingredient (ppm) | Preventive effect |
|---|---|---|
| 1 | 400 | 5 |
| 2 | 400 | 4 |
| 3 | 400 | 4 |
| 4 | 400 | 4 |
| 10 | 400 | 4 |
| 11 | 400 | 5 |
| 12 | 400 | 4 |
| 13 | 400 | 4 |
| 25 | 400 | 5 |
| 27 | 400 | 4 |
| 28 | 400 | 5 |
| 29 | 400 | 5 |
| 35 | 400 | 5 |
| 36 | 400 | 5 |
| 37 | 400 | 5 |
| 39 | 400 | 4 |
| 43 | 400 | 3 |
| 44 | 400 | 5 |
| 46 | 400 | 5 |
| 47 | 400 | 5 |
| 48 | 400 | 4 |
| 49 | 400 | 5 |
| 50 | 400 | 3 |
| 52 | 400 | 5 |
| 54 | 400 | 4 |
| 55 | 400 | 5 |
| 56 | 400 | 5 |
| 57 | 400 | 5 |
| 58 | 400 | 4 |
| 59 | 400 | 5 |
| 60 | 400 | 4 |
| 61 | 400 | 5 |
| 62 | 400 | 3 |
| 63 | 400 | 5 |
| 67 | 400 | 5 |
| 68 | 400 | 3 |
| 69 | 400 | 5 |
| 70 | 400 | 5 |
| 71 | 400 | 5 |
| 73 | 400 | 5 |
| 77 | 400 | 5 |
| 79 | 400 | 3 |
| 81 | 400 | 5 |
| 83 | 400 | 5 |
| 84 | 400 | 5 |
| 85 | 400 | 5 |
| 86 | 400 | 4 |
| 87 | 400 | 5 |
| 94 | 400 | 5 |
| 99 | 400 | 5 |
| 100 | 400 | 5 |
| 101 | 400 | 5 |
| 103 | 400 | 3 |
| 110 | 400 | 3 |
| 112 | 400 | 5 |
| 113 | 400 | 3 |
| 115 | 400 | 5 |

TABLE 6-continued

| Compound No. | Concentration of active ingredient (ppm) | Preventive effect |
|---|---|---|
| 121 | 400 | 4 |
| 133 | 400 | 5 |
| 135 | 400 | 5 |
| 136 | 400 | 3 |
| 138 | 400 | 4 |
| 144 | 400 | 4 |
| 146 | 400 | 5 |
| A | 400 | 0 |
| B | 400 | 0 |

TEST EXAMPLE 4

Preventive effect on anthracnose (*Colletotrichum lagenarium*) of cucumber

A plastic pot was filled with sandy soil, and seeds of cucumber (var: Sagamihanjiro) were sowed therein and grown in a greenhouse for 14 days until expansion of their cotyledons. The test compound formulated in a wettable powder according to Formulation Example 1 and diluted with water to a prescribed concentration was thoroughly sprayed over the seedlings, and a spore suspension of *Colletotrichum lagenarium* was inoculated thereto by spraying. The plants were kept at 23° C. under a humid condition for 1 day, further grown in the greenhouse for 4 days and subjected to observation for the preventive effect. The results are shown in Table 7.

TABLE 7

| Compound No. | Concentration of active ingredient (ppm) | Preventive effect |
|---|---|---|
| 1 | 400 | 5 |
| 2 | 400 | 4 |
| 3 | 400 | 5 |
| 4 | 400 | 5 |
| 5 | 400 | 4 |
| 6 | 400 | 4 |
| 8 | 400 | 4 |
| 9 | 400 | 5 |
| 10 | 400 | 5 |
| 12 | 400 | 5 |
| 13 | 400 | 4 |
| 14 | 400 | 4 |
| 15 | 400 | 4 |
| 16 | 400 | 4 |
| 19 | 400 | 5 |
| 20 | 400 | 4 |
| 23 | 400 | 4 |
| 24 | 400 | 4 |
| 25 | 400 | 5 |
| 26 | 400 | 4 |
| 29 | 400 | 4 |
| 30 | 400 | 4 |
| 31 | 400 | 5 |
| 32 | 400 | 5 |
| 33 | 400 | 4 |
| 35 | 400 | 4 |
| 36 | 400 | 5 |
| 37 | 400 | 5 |
| 38 | 400 | 5 |
| 39 | 400 | 5 |
| 41 | 400 | 5 |
| 42 | 400 | 5 |
| 43 | 400 | 4 |
| 44 | 400 | 5 |
| 46 | 400 | 5 |
| 47 | 400 | 4 |
| 49 | 400 | 5 |
| 50 | 400 | 5 |
| 51 | 400 | 5 |
| 52 | 400 | 5 |

TABLE 7-continued

| Compound No. | Concentration of active ingredient (ppm) | Preventive effect |
|---|---|---|
| 53 | 400 | 5 |
| 54 | 400 | 4 |
| 55 | 400 | 4 |
| 56 | 400 | 5 |
| 57 | 400 | 5 |
| 58 | 400 | 4 |
| 59 | 400 | 4 |
| 60 | 400 | 5 |
| 61 | 400 | 5 |
| 62 | 400 | 5 |
| 63 | 400 | 5 |
| 65 | 400 | 5 |
| 66 | 400 | 4 |
| 67 | 400 | 5 |
| 68 | 400 | 4 |
| 69 | 400 | 5 |
| 70 | 400 | 4 |
| 71 | 400 | 5 |
| 72 | 400 | 4 |
| 75 | 400 | 5 |
| 77 | 400 | 5 |
| 78 | 400 | 4 |
| 79 | 400 | 4 |
| 80 | 400 | 5 |
| 81 | 400 | 5 |
| 82 | 400 | 4 |
| 83 | 400 | 5 |
| 84 | 400 | 5 |
| 85 | 400 | 4 |
| 86 | 400 | 5 |
| 87 | 400 | 5 |
| 88 | 400 | 4 |
| 89 | 400 | 5 |
| 90 | 400 | 5 |
| 91 | 400 | 5 |
| 92 | 400 | 4 |
| 93 | 400 | 5 |
| 99 | 400 | 4 |
| 100 | 400 | 4 |
| 101 | 400 | 4 |
| 102 | 400 | 5 |
| 118 | 400 | 4 |
| 119 | 400 | 5 |
| 120 | 400 | 4 |
| 121 | 400 | 5 |
| 122 | 400 | 4 |
| 124 | 400 | 3 |
| 127 | 400 | 4 |
| 130 | 400 | 4 |
| 132 | 400 | 4 |
| 133 | 400 | 5 |
| 134 | 400 | 4 |
| 135 | 400 | 5 |
| 136 | 400 | 4 |
| 138 | 400 | 5 |
| 142 | 400 | 4 |
| 146 | 400 | 4 |
| 158 | 400 | 4 |
| 160 | 400 | 5 |
| A | 400 | 0 |
| B | 400 | 2 |

TEST EXAMPLE 5

Preventive effect on scab (*Venturia inaequalis*) of apple

A plastic pot was filled with sandy soil, and seeds of apple (var: Fuji) were sowed therein and grown in a greenhouse for 20 days until expansion of their 4 to 5-leaves. The test compound formulated in a suspension according to Formulation Example 2 and diluted with water to a prescribed concentration was thoroughly sprayed to the seedlings of the test plants and, a spore suspension of *Venturia inaequalis* was inoculated thereto by spraying. The plants were kept at 15° C. under a humid condition for 4 days, further grown under illumination for 15 days and subjected to observation for the preventive effect. The results are shown in Table 8.

TABLE 8

| Compound No. | Concentration of active ingredient (ppm) | Controlling effect |
|---|---|---|
| 1 | 200 | 5 |
| 3 | 200 | 5 |
| 4 | 200 | 5 |
| 5 | 200 | 5 |
| 6 | 200 | 5 |
| 10 | 200 | 5 |
| 11 | 200 | 4 |
| 12 | 200 | 4 |
| 13 | 200 | 4 |
| 25 | 200 | 5 |
| 28 | 200 | 4 |
| 29 | 200 | 5 |
| 32 | 200 | 5 |
| 35 | 200 | 5 |
| 36 | 200 | 5 |
| 39 | 200 | 5 |
| 41 | 200 | 4 |
| 42 | 200 | 5 |
| 46 | 200 | 5 |
| 47 | 200 | 5 |
| 51 | 200 | 4 |
| 52 | 200 | 5 |
| 53 | 200 | 4 |
| 54 | 200 | 5 |
| 55 | 200 | 5 |
| 56 | 200 | 5 |
| 57 | 200 | 5 |
| 58 | 200 | 4 |
| 59 | 200 | 5 |
| 60 | 200 | 5 |
| 62 | 200 | 5 |
| 63 | 200 | 5 |
| 65 | 200 | 5 |
| 66 | 200 | 5 |
| 67 | 200 | 5 |
| 68 | 200 | 5 |
| 72 | 200 | 5 |
| 74 | 200 | 5 |
| 75 | 200 | 5 |
| 77 | 200 | 5 |
| 79 | 200 | 5 |
| 80 | 200 | 5 |
| 83 | 200 | 5 |
| 84 | 200 | 5 |
| 85 | 200 | 5 |
| 86 | 200 | 5 |
| 87 | 200 | 5 |
| 88 | 200 | 5 |
| 89 | 200 | 5 |
| 90 | 200 | 5 |
| 91 | 200 | 5 |
| 92 | 200 | 5 |
| 93 | 200 | 5 |
| 94 | 200 | 5 |
| 97 | 200 | 5 |
| 99 | 200 | 5 |
| 100 | 200 | 5 |
| 101 | 200 | 4 |
| 102 | 200 | 5 |
| 104 | 200 | 5 |
| 105 | 200 | 5 |
| 114 | 200 | 5 |
| 115 | 200 | 5 |
| 116 | 200 | 5 |
| 117 | 200 | 5 |
| 118 | 200 | 5 |
| 119 | 200 | 5 |
| 120 | 200 | 5 |
| 121 | 200 | 5 |
| 122 | 200 | 5 |
| 124 | 200 | 5 |
| 126 | 200 | 5 |
| 128 | 200 | 4 |
| 129 | 200 | 5 |
| 130 | 200 | 5 |
| 133 | 200 | 5 |

TABLE 8-continued

| Compound No. | Concentration of active ingredient (ppm) | Controlling effect |
|---|---|---|
| 135 | 200 | 5 |
| 136 | 200 | 5 |
| 137 | 200 | 5 |
| 142 | 200 | 5 |
| 143 | 200 | 5 |
| 144 | 200 | 5 |
| 145 | 200 | 4 |
| 146 | 200 | 5 |
| 147 | 200 | 5 |
| 149 | 200 | 5 |
| 151 | 200 | 5 |
| A | 200 | 0 |
| B | 200 | 2 |

TEST EXAMPLE 6

Preventive effect on brown spot (*Cercospora arachidicola*) of peanuts

A plastic pot was filled with sandy soil, and peanuts (var: Chibahanryusei) were sowed therein and grown in a greenhouse for 14 days. The test compound formulated in an emulsifiable concentrate according to Formulation Example 4 and diluted with water to a prescribed concentration was thoroughly sprayed over the seedlings of the test plants and, after air-drying, a spore suspension of *Cercospora arachidicola* was inoculated thereto by spraying. The plants were kept at 23° C. under a humid condition for 7 days, further grown in the greenhouse for 7 days and subjected to observation for the preventive effect. The results are shown in Table 9.

TABLE 9

| Compound No. | Concentration of active ingredient (ppm) | Preventive effect |
|---|---|---|
| 3 | 200 | 5 |
| 8 | 200 | 4 |
| 25 | 200 | 3 |
| 33 | 200 | 4 |
| 35 | 200 | 5 |
| 36 | 200 | 5 |
| 37 | 200 | 5 |
| 38 | 200 | 5 |
| 39 | 200 | 5 |
| 41 | 200 | 5 |
| 44 | 200 | 5 |
| 45 | 200 | 5 |
| 46 | 200 | 5 |
| 48 | 200 | 5 |
| 49 | 200 | 5 |
| 54 | 200 | 5 |
| 59 | 200 | 5 |
| 63 | 200 | 5 |
| 78 | 200 | 5 |
| 79 | 200 | 5 |
| 80 | 200 | 5 |
| 83 | 200 | 5 |
| 84 | 200 | 5 |
| 85 | 200 | 5 |
| 86 | 200 | 5 |
| 87 | 200 | 5 |
| 91 | 200 | 5 |
| 102 | 200 | 5 |
| 103 | 200 | 5 |
| 104 | 200 | 5 |
| 105 | 200 | 5 |
| 110 | 200 | 5 |
| 111 | 200 | 5 |
| 112 | 200 | 5 |
| 115 | 200 | 5 |
| 116 | 200 | 5 |

TABLE 9-continued

| Compound No. | Concentration of active ingredient (ppm) | Preventive effect |
|---|---|---|
| 117 | 200 | 5 |
| 118 | 200 | 5 |
| 119 | 200 | 5 |
| 120 | 200 | 5 |
| 121 | 200 | 5 |
| 128 | 200 | 5 |
| 144 | 200 | 4 |
| 149 | 200 | 4 |
| 150 | 200 | 5 |
| 151 | 200 | 5 |
| 158 | 200 | 5 |
| 160 | 200 | 4 |
| A | 200 | 0 |
| B | 200 | 0 |

TEST EXAMPLE 7

Preventive effect on sheath blight (*Rhizoctonia solani*) of rice plants

A plastic pot was filled with sandy soil, and seeds of rice plants (var: Kinki No. 33) were sowed therein and grown in a greenhouse for 28 days. The test compound formulated in an emulsifiable concentrate according to Formulation Example 4 and diluted with water to a prescribed concentration was thoroughly sprayed over the seedlings of the rice plants and, after air-drying, an agar suspension containing spores of *Rhizoctonia solani* was inoculated thereto by spraying. The plants were kept at 28° C. under dark and humid conditions for 4 days and subjected to observation for the preventive effect. The results are shown in Table 10.

TABLE 10

| Compound No. | Concentration of active ingredient (ppm) | Preventive effect |
|---|---|---|
| 1 | 200 | 5 |
| 2 | 200 | 5 |
| 9 | 200 | 5 |
| 10 | 200 | 5 |
| 11 | 200 | 5 |
| 12 | 200 | 5 |
| 13 | 200 | 5 |
| 14 | 200 | 5 |
| 25 | 200 | 5 |
| 70 | 200 | 4 |
| 75 | 200 | 4 |
| 110 | 200 | 4 |
| 126 | 200 | 5 |
| 127 | 200 | 5 |
| 130 | 200 | 5 |
| 131 | 200 | 5 |
| 132 | 200 | 5 |
| 136 | 200 | 5 |
| 137 | 200 | 5 |
| 138 | 200 | 5 |
| A | 200 | 0 |
| B | 200 | 2 |

TEST EXAMPLE 8

Preventive effect on stripe diseases (*Pyrenophora teres*) of barley

A plastic pot was filled with sandy soil, and seeds of barley (var: Sekijinriki) were sowed therein and grown in a greenhouse for 7 days. The test compound formulated in an emulsifiable concentrate according to Formulation Example 4 and diluted with water to a prescribed concentration was thoroughly sprayed over the seedlings of the test plants and, after air-drying, a spore suspension of *Purenophora teres* was inoculated thereto by spraying. The plants were kept at 15° C. under a humid condition for 1 day, taken out from the humid condition, then grown at 15° C. for 17 days and subjected to observation for the preventive effect. The results are shown in Table 11.

TABLE 11

| Compound No. | Concentration of active ingredient (ppm) | Preventive effect |
|---|---|---|
| 1 | 400 | 5 |
| 35 | 400 | 5 |
| 36 | 400 | 5 |
| 43 | 400 | 5 |
| 44 | 400 | 4 |
| 45 | 400 | 4 |
| 46 | 400 | 5 |
| 47 | 400 | 5 |
| 48 | 400 | 4 |
| 49 | 400 | 4 |
| 51 | 400 | 4 |
| 52 | 400 | 4 |
| 53 | 400 | 5 |
| 55 | 400 | 5 |
| 56 | 400 | 4 |
| 57 | 400 | 5 |
| 58 | 400 | 4 |
| 59 | 400 | 4 |
| 60 | 400 | 4 |
| 61 | 400 | 5 |
| 62 | 400 | 4 |
| 63 | 400 | 4 |
| 65 | 400 | 4 |
| 66 | 400 | 5 |
| 67 | 400 | 5 |
| 68 | 400 | 5 |
| 69 | 400 | 5 |
| 70 | 400 | 5 |
| 71 | 400 | 4 |
| 72 | 400 | 4 |
| 73 | 400 | 5 |
| 74 | 400 | 5 |
| 75 | 400 | 5 |
| 77 | 400 | 5 |
| 78 | 400 | 4 |
| 79 | 400 | 5 |
| 80 | 400 | 5 |
| 81 | 400 | 5 |
| 82 | 400 | 5 |
| 83 | 400 | 5 |
| 84 | 400 | 5 |
| 85 | 400 | 5 |
| 86 | 400 | 4 |
| 87 | 400 | 5 |
| 88 | 400 | 5 |
| 89 | 400 | 5 |
| 91 | 400 | 5 |
| 92 | 400 | 5 |
| 94 | 400 | 5 |
| 95 | 400 | 5 |
| 96 | 400 | 5 |
| 99 | 400 | 3 |
| 100 | 400 | 5 |
| 102 | 400 | 5 |
| 103 | 400 | 4 |
| 104 | 400 | 5 |
| 105 | 400 | 5 |
| 110 | 400 | 5 |
| 111 | 400 | 5 |
| 112 | 400 | 5 |
| 113 | 400 | 5 |
| 114 | 400 | 4 |
| 115 | 400 | 5 |
| 116 | 400 | 5 |
| 117 | 400 | 5 |
| 118 | 400 | 5 |
| 119 | 400 | 5 |
| 120 | 400 | 5 |
| 121 | 400 | 5 |
| 128 | 400 | 5 |
| 129 | 400 | 5 |
| 135 | 400 | 5 |
| 136 | 400 | 5 |
| 137 | 400 | 5 |
| 138 | 400 | 5 |
| 139 | 400 | 5 |
| 142 | 400 | 4 |
| 143 | 400 | 5 |
| 144 | 400 | 5 |
| 146 | 400 | 5 |
| 147 | 400 | 5 |
| 148 | 400 | 4 |
| 149 | 400 | 5 |
| 150 | 400 | 5 |
| 151 | 400 | 5 |
| 160 | 400 | 4 |
| A | 400 | 0 |
| B | 400 | 0 |

TEST EXAMPLE 9

Preventive effect on leaf bloth (*Rhynchosporium secalis*) of barley

A plastic pot was filled with sandy soil, and seeds of barley (var: Sekisinriki) were sowed therein and grown in a greenhouse for 10 days. The test compound formulated in an emulsifiable concentrate according to Formulation Example 4 and diluted with water to a prescribed concentration was thoroughly sprayed over the seedlings of the test plants and, after air-drying, a spore suspension of *Rhynchosporium secalis* was inoculated thereto by spraying. The plants were kept at 15° C. for 7 under dark and humid conditions for 1 day and further under illumination for 14 days and subjected to observation for the preventive effect. The results are shown in Table 12.

TABLE 12

| Compound No. | Concentration of active ingredient (ppm) | Preventive effect |
|---|---|---|
| 1 | 200 | 5 |
| 35 | 200 | 5 |
| 36 | 200 | 5 |
| 45 | 200 | 5 |
| 46 | 200 | 5 |
| 47 | 200 | 5 |
| 63 | 200 | 5 |
| 66 | 200 | 5 |
| 68 | 200 | 3 |
| 72 | 200 | 3 |
| 74 | 200 | 5 |
| 75 | 200 | 5 |
| 79 | 200 | 3 |
| 82 | 200 | 5 |
| 83 | 200 | 5 |
| 84 | 200 | 5 |
| 85 | 200 | 5 |
| 86 | 200 | 5 |
| 87 | 200 | 4 |
| 88 | 200 | 3 |
| 94 | 200 | 5 |
| 95 | 200 | 5 |
| 96 | 200 | 5 |
| 104 | 200 | 3 |
| 105 | 200 | 5 |
| 110 | 200 | 4 |
| 112 | 200 | 5 |
| 113 | 200 | 5 |
| 115 | 200 | 5 |
| 116 | 200 | 5 |
| 117 | 200 | 5 |

TABLE 12-continued

| Compound No. | Concentration of active ingredient (ppm) | Preventive effect |
|---|---|---|
| 118 | 200 | 5 |
| 119 | 200 | 5 |
| 120 | 200 | 5 |
| 121 | 200 | 5 |
| 128 | 200 | 5 |
| 135 | 200 | 5 |
| 136 | 200 | 4 |
| 139 | 200 | 4 |
| 143 | 200 | 4 |
| 144 | 200 | 5 |
| 145 | 200 | 5 |
| 146 | 200 | 5 |
| 147 | 200 | 4 |
| 151 | 200 | 5 |
| A | 200 | 0 |
| B | 200 | 1 |

TEST EXAMPLE 10

Preventive effect on (*Pseudocercosporella herpotrichoides*) of wheat

A plastic pot was filled with sandy soil, and seeds of wheat (var: Nohrin No. 73) were sowed therein and grown in a greenhouse for 10 days. The test compound formulated in an emulsifiable concentrate according to Formulation Example 4 and diluted with water to a prescribed concentration was thoroughly sprayed over the seedlings of the test plants and, after air-drying, a spore suspension of *Pseudocercosporella herpotrichloides* was inoculated thereto by spraying. The plants were kept at 15° C. under dark and humid conditions for 4 days, further under illuminated and humid conditions for 4 days and subjected to observation for the preventive effect. The results are shown in Table 13.

TABLE 13

| Compound No. | Concentration of active ingredient (ppm) | Preventive effect |
|---|---|---|
| 59 | 200 | 5 |
|  | 100 | 5 |
|  | 50 | 2 |
| 63 | 200 | 5 |
|  | 100 | 5 |
|  | 50 | 4 |
| A | 400 | 0 |
| B | 400 | 0 |

What is claimed is:

1. A compound of the formula:

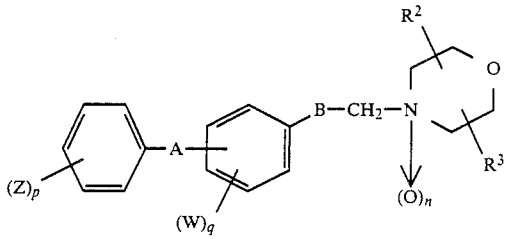

wherein
A is oxygen or sulfur;
B is —CH$_2$—CHR$^1$— or —CH=CR$^1$— wherein R$^1$ is H or CH$_3$;
W is, the same or different, hydrogen, halogen, a lower alkyl group or a lower alkoxy group;
R$^2$ is hydrogen, a lower alkyl group, a lower alkoxy group, a lower alkoxy(lower)alkyl group, a hydroxyl group or a hydroxy(lower)alkyl group;
R$^3$ is hydrogen or a lower alkyl group;
n is an integer of 0 or 1;
Z is, the same or different, hydrogen, halogen, a lower alkyl group, a lower alkoxy group, a halo(lower)alkyl group, a halo(lower)alkoxy group, a nitro group, a methylenedioxy group or a cyano group;
p is an integer of 0 to 5; and
q is an integer of 0 or 1, or its salt.

2. The compound according to claim 1, wherein R$^2$ is hydrogen, a C$_1$-C$_2$ alkyl group, a C$_1$-C$_2$ alkoxy group, a C$_1$-C$_2$ alkoxy(C$_1$-C$_2$)alkyl group, a hydroxy group or a hydroxy(C$_1$-C$_2$)alkyl group;
R$^3$ is hydrogen or methyl;
n is an integer of 0 or 1;
q is 0;
Z is, the same or different, hydrogen, halogen, a C$_1$-C$_4$ alkyl group, a C$_1$-C$_2$ alkoxy group, a halo(C$_1$-C$_2$)alkyl group, a halo(C$_1$-C$_2$)alkoxy group, a nitro group, a methylenedioxy group, or a cyano group;
p is an integer of 0 to 5; and
A and B are as defined in claim 1.

3. The compound according to claim 2, wherein Z is, the same or different, hydrogen, halogen, a C$_1$-C$_4$ alkyl group, a methoxy group, a trifluoromethyl group, a halo(C$_1$-C$_2$)alkoxy group, a nitro group, a methylenedioxy group, or a cyano group.

4. The compounding according to claim 1, wherein A is oxygen.

5. A fungicidal composition which comprises a fungicidally effective amount of a compound according to claim 1.

6. A method for controlling fungi which comprises applying a fungicidally effective amount of a compound according to claim 1 to said fungi.

7. The method according to claim 6, wherein said fungi are plant pathogenic fungi.

8. The compounding according to claim 1, wherein B is —CH$_2$—CH(CH$_3$)—.

9. The compounding according to claim 8, which has the following formula:

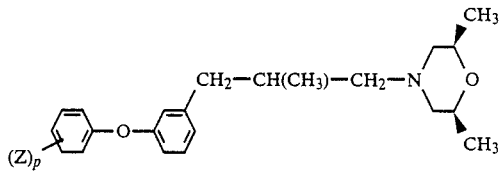

wherein Z and p are as defined in claim 8.

* * * * *